United States Patent
Ackerman et al.

(10) Patent No.: US 11,952,425 B2
(45) Date of Patent: Apr. 9, 2024

(54) HIGH AFFINITY B7-H6 ANTIBODIES AND ANTIBODY FRAGMENTS

(71) Applicant: TRUSTEES OF DARTMOUTH COLLEGE, Hanover, NH (US)

(72) Inventors: Margaret Ackerman, Lebanon, NH (US); Casey Hua, Hanover, NH (US); Charles Sentman, Hanover, NH (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 377 days.

(21) Appl. No.: 17/318,310

(22) Filed: May 12, 2021

(65) Prior Publication Data
US 2021/0340258 A1 Nov. 4, 2021

Related U.S. Application Data

(62) Division of application No. 16/092,681, filed as application No. PCT/US2017/027615 on Apr. 14, 2017, now Pat. No. 11,034,767.

(60) Provisional application No. 62/323,039, filed on Apr. 15, 2016.

(51) Int. Cl.
| | |
|---|---|
| *C07K 16/28* | (2006.01) |
| *A61K 47/68* | (2017.01) |
| *A61K 51/10* | (2006.01) |
| *A61P 35/00* | (2006.01) |
| *C07K 14/705* | (2006.01) |
| *C07K 14/725* | (2006.01) |
| *C07K 16/46* | (2006.01) |

(52) U.S. Cl.
CPC ...... *C07K 16/2827* (2013.01); *A61K 47/6803* (2017.08); *A61K 47/6849* (2017.08); *A61K 51/1027* (2013.01); *A61K 51/1093* (2013.01); *A61P 35/00* (2018.01); *C07K 14/7051* (2013.01); *C07K 14/70517* (2013.01); *C07K 14/70521* (2013.01); *C07K 16/2809* (2013.01); *C07K 16/468* (2013.01); *C07K 2317/21* (2013.01); *C07K 2317/31* (2013.01); *C07K 2317/56* (2013.01); *C07K 2317/622* (2013.01); *C07K 2317/73* (2013.01); *C07K 2317/92* (2013.01); *C07K 2319/02* (2013.01); *C07K 2319/03* (2013.01); *C07K 2319/033* (2013.01)

(58) Field of Classification Search
CPC ............ C07K 16/2827; C07K 14/7051; C07K 14/70517; C07K 14/70521; C07K 16/2809; C07K 16/468; C07K 2317/21; C07K 2317/31; C07K 2317/56; C07K 2317/622; A61K 47/6803; A61K 47/6849; A61K 51/1027; A61K 51/1093; A61P 35/00
See application file for complete search history.

(56) References Cited

U.S. PATENT DOCUMENTS

2013/0004432 A1* 1/2013 Pierres ............... A61P 35/00
424/9.4
2015/0152181 A1 6/2015 Sentman et al.

* cited by examiner

*Primary Examiner* — Nelson B Moseley, II
(74) *Attorney, Agent, or Firm* — Robin L. Teskin; Baker, Donelson, Bearman, Caldwell & Berkowitz PC

(57) ABSTRACT

Provided herein, in some embodiments, are antibodies, antigen-binding antibody fragments, chimeric antigen receptors (CARs) and bispecific T cell engagers (BiTEs) that bind specifically to B7 homolog 6. Also provided herein are methods of using the same and cells comprising the same.

21 Claims, 10 Drawing Sheets
Specification includes a Sequence Listing.

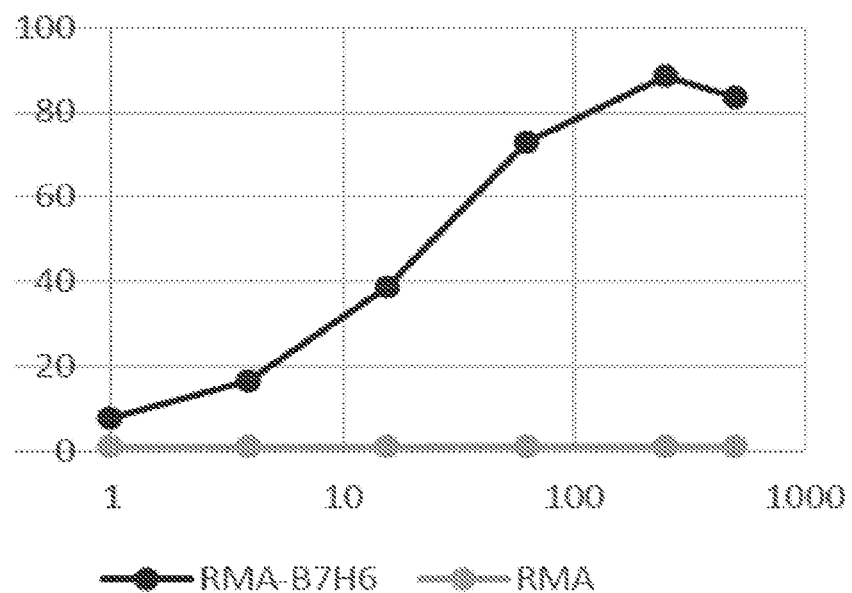

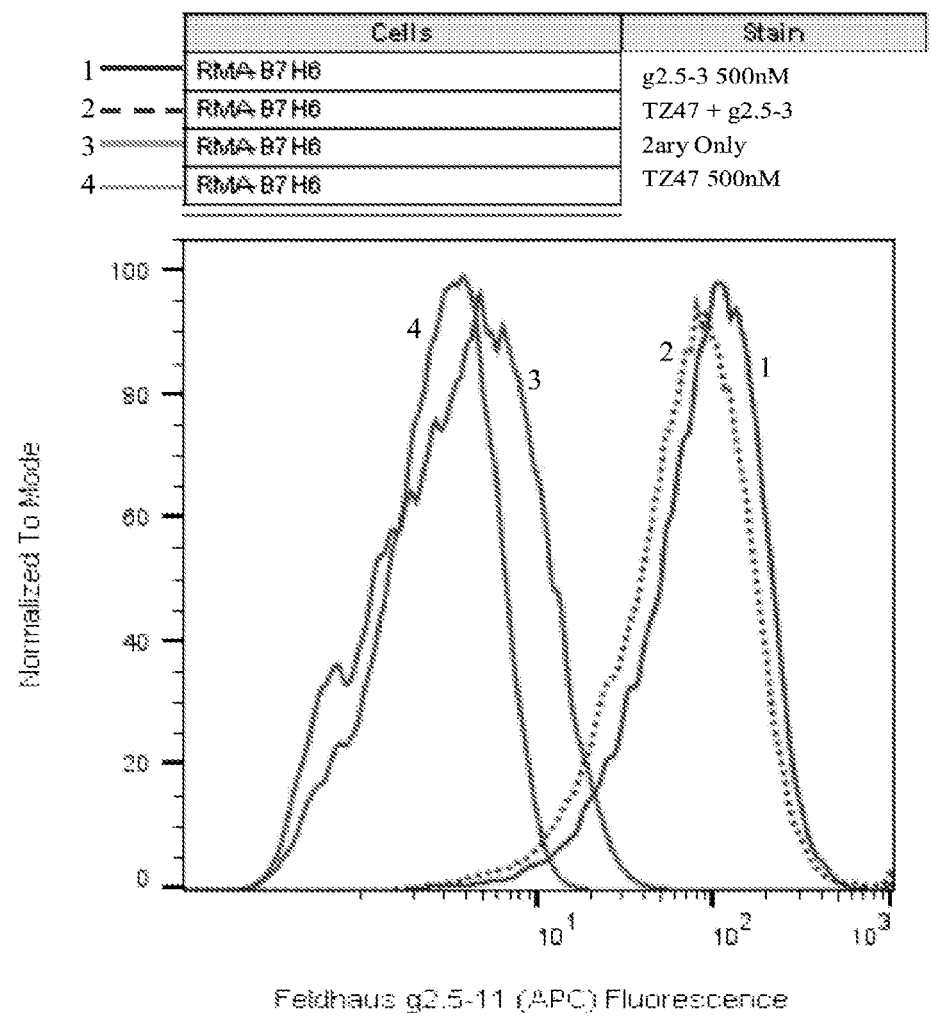

SEQUENCE LISTING

<160> NUMBER OF SEQ ID NOS: 42

<210> SEQ ID NO 1
<211> LENGTH: 252
<212> TYPE: PRT
<213> ORGANISM: Artificial Sequence
<220> FEATURE:
<223> OTHER INFORMATION: Synthetic Polypeptide

<400> SEQUENCE: 1

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Leu Gly Thr Tyr
            20                  25                  30

Thr Leu His Trp Met Arg Gln Ala Pro Gly Gln Arg Ile Glu Trp Met
        35                  40                  45

Gly Trp Ile Asn Pro Gly Asn Gly Tyr Thr Lys Tyr Ser Gln Arg Leu
    50                  55                  60

Gln Gly Arg Val Thr Ile Asn Arg Asp Thr Ser Ala Thr Thr Thr Tyr
65                  70                  75                  80

Met Glu Leu Ser Ser Leu Arg Ser Glu Asp Thr Ala Val Tyr Phe Cys
                85                  90                  95

Ala Thr Asp Arg Ala Pro Val Arg Arg Ala Phe Asp Ile Trp Gly Gln
            100                 105                 110

Gly Thr Met Val Thr Val Ser Ser Gly Ile Leu Gly Ser Gly Gly Gly
        115                 120                 125

Gly Ser Gly Gly Gly Gly Ser Gly Gly Gly Gly Ser Gln Ser Val Leu
    130                 135                 140

Thr Gln Pro Ala Ser Val Ser Gly Ser Pro Gly Gln Ser Val Thr Ile
145                 150                 155                 160

Ser Cys Thr Gly Thr Ser Ser Asp Ile Gly Ser Tyr Lys Phe Val Ser
                165                 170                 175
```

```
Trp Tyr Gln His His Pro Gly Lys Ala Pro Lys Leu Met Ile Tyr Asp
                180                 185                 190

Val Thr Gln Arg Pro Ser Gly Val Pro Tyr Arg Phe Ser Gly Ser Lys
            195                 200                 205

Ser Gly Asn Thr Ala Ser Leu Thr Ile Ser Gly Leu Gln Ala Glu Asp
        210                 215                 220

Glu Ala Asp Tyr Tyr Cys Cys Ser Tyr Ala Gly Asp Tyr Thr Tyr Ala
225                 230                 235                 240

Leu Phe Gly Gly Gly Thr Gln Leu Thr Val Leu Ser
                245                 250

<210> SEQ ID NO 2
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 2

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Leu Gly Thr Tyr
            20                  25                  30

Thr Leu His Trp Met Arg Gln Ala Pro Gly Gln Arg Ile Glu Trp Met
        35                  40                  45

Gly Trp Ile Asn Pro Gly Asn Gly Tyr Thr Lys Tyr Ser Gln Arg Leu
    50                  55                  60

Gln Gly Arg Val Thr Ile Asn Arg Asp Thr Ser Ala Thr Thr Thr Tyr
65                  70                  75                  80

Met Glu Leu Ser Ser Leu Arg Ser Glu Asp Thr Ala Val Tyr Phe Cys
                85                  90                  95

Ala Thr Asp Arg Ala Pro Val Arg Arg Ala Phe Asp Ile Trp Gly Gln
            100                 105                 110

Gly Thr Met Val Thr Val Ser Ser
        115                 120

<210> SEQ ID NO 3
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 3

Gln Ser Val Leu Thr Gln Pro Ala Ser Val Ser Gly Ser Pro Gly Gln
1               5                   10                  15

Ser Val Thr Ile Ser Cys Thr Gly Thr Ser Ser Asp Ile Gly Ser Tyr
            20                  25                  30

Lys Phe Val Ser Trp Tyr Gln His His Pro Gly Lys Ala Pro Lys Leu
        35                  40                  45

Met Ile Tyr Asp Val Thr Gln Arg Pro Ser Gly Val Pro Tyr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
                85                  90                  95

Tyr Thr Tyr Ala Leu Phe Gly Gly Gly Thr Gln Leu Thr Val Leu Ser
```

<210> SEQ ID NO 4
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 4

Gly Tyr Thr Leu Gly Thr Tyr Thr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 5

Ile Asn Pro Gly Asn Gly Tyr Thr
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 6

Ala Thr Asp Arg Ala
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 7

Ser Ser Asp Ile Gly Ser Tyr Lys Phe
1               5

<210> SEQ ID NO 8
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 8

Asp Val Thr
1

<210> SEQ ID NO 9
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 9

Cys Ser Tyr Ala Gly Asp Tyr Thr Tyr Ala Leu
1               5                   10

```
<210> SEQ ID NO 10
<211> LENGTH: 252
<212> TYPE: PRT
<213> ORGANISM: Artificial Sequence
<220> FEATURE:
<223> OTHER INFORMATION: Synthetic Polypeptide

<400> SEQUENCE: 10

Gln Val Gln Leu Val Gln Ser Gly Ala Glu Val Lys Lys Pro Gly Ala
1               5                   10                  15

Ser Val Lys Ile Pro Cys Lys Ala Ser Gly Tyr Thr Leu Gly Thr Tyr
            20                  25                  30

Thr Leu His Trp Met Arg Gln Ala Pro Gly Gln Arg Ile Glu Trp Met
        35                  40                  45

Gly Trp Ile Asn Pro Gly Asn Gly Tyr Thr Lys Tyr Ser Gln Arg Phe
    50                  55                  60

Gln Gly Arg Val Thr Ile Asn Arg Asp Thr Ser Ala Thr Thr Thr Tyr
65                  70                  75                  80

Met Glu Leu Ser Ser Leu Arg Ser Glu Asp Thr Ala Val Tyr Phe Cys
                85                  90                  95

Ala Thr Asp Arg Ala Pro Val Arg Arg Ala Phe Asp Ile Trp Gly Gln
            100                 105                 110

Gly Thr Met Val Thr Val Ser Ser Gly Ile Leu Gly Ser Gly Gly Gly
        115                 120                 125

Gly Ser Gly Gly Gly Gly Ser Gly Gly Gly Gly Ser Gln Ser Val Leu
    130                 135                 140

Thr Gln Pro Ala Ser Val Ser Gly Ser Pro Gly Gln Ser Val Thr Ile
145                 150                 155                 160

Ser Cys Thr Gly Thr Ser Ser Asp Ile Gly Ser Tyr Lys Phe Val Ser
                165                 170                 175

Trp Tyr Gln His His Pro Gly Lys Ala Pro Lys Leu Met Ile Tyr Asp
            180                 185                 190

Val Thr Gln Arg Pro Ser Gly Val Pro Tyr Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Cys Leu Tyr Ala Gly Asp Tyr Thr Tyr Ala
225                 230                 235                 240

Leu Phe Gly Gly Gly Thr Gln Leu Thr Val Leu Ser
                245                 250

<210> SEQ ID NO 11
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 11

Gln Val Gln Leu Val Gln Ser Gly Ala Glu Val Lys Lys Pro Gly Ala
1               5                   10                  15

Ser Val Lys Ile Pro Cys Lys Ala Ser Gly Tyr Thr Leu Gly Thr Tyr
            20                  25                  30

Thr Leu His Trp Met Arg Gln Ala Pro Gly Gln Arg Ile Glu Trp Met
        35                  40                  45

Gly Trp Ile Asn Pro Gly Asn Gly Tyr Thr Lys Tyr Ser Gln Arg Phe
```

```
                    50                  55                  60
Gln Gly Arg Val Thr Ile Asn Arg Asp Thr Ser Ala Thr Thr Thr Tyr
 65                  70                  75                  80

Met Glu Leu Ser Ser Leu Arg Ser Glu Asp Thr Ala Val Tyr Phe Cys
                 85                  90                  95

Ala Thr Asp Arg Ala Pro Val Arg Arg Ala Phe Asp Ile Trp Gly Gln
            100                 105                 110

Gly Thr Met Val Thr Val Ser Ser
        115                 120

<210> SEQ ID NO 12
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 12

Gln Ser Val Leu Thr Gln Pro Ala Ser Val Ser Gly Ser Pro Gly Gln
  1               5                  10                  15

Ser Val Thr Ile Ser Cys Thr Gly Thr Ser Ser Asp Ile Gly Ser Tyr
                 20                  25                  30

Lys Phe Val Ser Trp Tyr Gln His Pro Gly Lys Ala Pro Lys Leu
             35                  40                  45

Met Ile Tyr Asp Val Thr Gln Arg Pro Ser Gly Val Pro Tyr Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Leu Tyr Ala Gly Asp
                 85                  90                  95

Tyr Thr Tyr Ala Leu Phe Gly Gly Gly Thr Gln Leu Thr Val Leu Ser
            100                 105                 110

<210> SEQ ID NO 13
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 13

Gly Tyr Thr Leu Gly Thr Tyr Thr
  1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 14

Ile Asn Pro Gly Asn Gly Tyr Thr
  1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Polypeptide
```

```
<400> SEQUENCE: 15

Ala Thr Asp Arg Ala
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 16

Ser Ser Asp Ile Gly Ser Tyr Lys Phe
1               5

<210> SEQ ID NO 17
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 17

Asp Val Thr
1

<210> SEQ ID NO 18
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 18

Cys Leu Tyr Ala Gly Asp Tyr Thr Tyr Ala Leu
1               5                   10

<210> SEQ ID NO 19
<211> LENGTH: 252
<212> TYPE: PRT
<213> ORGANISM: Artificial Sequence
<220> FEATURE:
<223> OTHER INFORMATION: Synthetic Polypeptide

<400> SEQUENCE: 19

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Leu Gly Thr Tyr
            20                  25                  30

Thr Leu His Trp Met Arg Gln Ala Pro Gly Gln Arg Ile Glu Trp Met
        35                  40                  45

Gly Trp Ile Asn Pro Gly Asn Gly Tyr Thr Lys Tyr Ser Gln Arg Phe
    50                  55                  60

Gln Gly Arg Val Thr Ile Asn Arg Asp Thr Ser Ala Thr Thr Thr Tyr
65                  70                  75                  80

Met Glu Leu Ser Ser Leu Arg Ser Glu Asp Thr Ala Val Tyr Phe Cys
                85                  90                  95

Ala Thr Asp Arg Ala Pro Val Arg Arg Ala Phe Asp Ile Trp Gly Gln
            100                 105                 110

Gly Thr Met Val Thr Val Ser Ser Gly Ile Leu Gly Ser Gly Gly
        115                 120                 125

Gly Ser Gly Gly Gly Gly Ser Gly Gly Gly Gly Ser Gln Ser Val Leu
```

```
                130                 135                 140
Thr Gln Pro Ala Ser Val Ser Gly Ser Pro Gly Gln Ser Val Thr Ile
145                 150                 155                 160

Ser Cys Thr Gly Thr Ser Ser Asp Ile Gly Ser Tyr Lys Phe Val Ser
                165                 170                 175

Trp Tyr Gln His His Pro Gly Lys Ala Pro Lys Leu Met Ile Tyr Asp
                180                 185                 190

Val Thr Gln Arg Pro Ser Gly Val Pro Tyr Arg Phe Ser Gly Ser Lys
                195                 200                 205

Ser Gly Asn Thr Ala Ser Leu Thr Ile Ser Gly Leu Gln Ala Glu Asp
                210                 215                 220

Glu Ala Asp Tyr Tyr Cys Cys Ser Tyr Ala Gly Asp Tyr Thr Tyr Ala
225                 230                 235                 240

Leu Phe Gly Gly Gly Thr Gln Leu Thr Val Leu Ser
                245                 250

<210> SEQ ID NO 20
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 20

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Leu Gly Thr Tyr
                20                  25                  30

Thr Leu His Trp Met Arg Gln Ala Pro Gly Gln Arg Ile Glu Trp Met
            35                  40                  45

Gly Trp Ile Asn Pro Gly Asn Gly Tyr Thr Lys Tyr Ser Gln Arg Phe
        50                  55                  60

Gln Gly Arg Val Thr Ile Asn Arg Asp Thr Ser Ala Thr Thr Thr Tyr
65                  70                  75                  80

Met Glu Leu Ser Ser Leu Arg Ser Glu Asp Thr Ala Val Tyr Phe Cys
                85                  90                  95

Ala Thr Asp Arg Ala Pro Val Arg Arg Ala Phe Asp Ile Trp Gly Gln
                100                 105                 110

Gly Thr Met Val Thr Val Ser Ser
            115                 120

<210> SEQ ID NO 21
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 21

Gln Ser Val Leu Thr Gln Pro Ala Ser Val Ser Gly Ser Pro Gly Gln
1               5                   10                  15

Ser Val Thr Ile Ser Cys Thr Gly Thr Ser Ser Asp Ile Gly Ser Tyr
                20                  25                  30

Lys Phe Val Ser Trp Tyr Gln His His Pro Gly Lys Ala Pro Lys Leu
            35                  40                  45

Met Ile Tyr Asp Val Thr Gln Arg Pro Ser Gly Val Pro Tyr Arg Phe
        50                  55                  60
```

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Asp
                 85                  90                  95

Tyr Thr Tyr Ala Leu Phe Gly Gly Gly Thr Gln Leu Thr Val Leu Ser
            100                 105                 110

<210> SEQ ID NO 22
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 22

Gly Tyr Thr Leu Gly Thr Tyr Thr
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 23

Ile Asn Pro Gly Asn Gly Tyr Thr
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 24

Ala Thr Asp Arg Ala
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 25

Ser Ser Asp Ile Gly Ser Tyr Lys Phe
1               5

<210> SEQ ID NO 26
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 26

Asp Val Thr
1

<210> SEQ ID NO 27
<211> LENGTH: 11
<212> TYPE: PRT
<213> ORGANISM: Artificial Sequence

```
<220> FEATURE:
<223> OTHER INFORMATION: Synthetic Polypeptide

<400> SEQUENCE: 27

Cys Ser Tyr Ala Gly Asp Tyr Thr Tyr Ala Leu
1               5                   10

<210> SEQ ID NO 28
<211> LENGTH: 252
<212> TYPE: PRT
<213> ORGANISM: Artificial Sequence
<220> FEATURE:
<223> OTHER INFORMATION: Synthetic Polypeptide

<400> SEQUENCE: 28

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Pro Gly Thr Tyr
                20                  25                  30

Thr Leu His Trp Met Arg Gln Ala Pro Gly Gln Arg Ile Glu Trp Met
            35                  40                  45

Gly Trp Ile Asn Pro Gly Asn Gly Tyr Thr Lys Tyr Ser Gln Arg Phe
        50                  55                  60

Gln Ala Arg Val Thr Ile Asn Arg Asp Thr Ser Ala Thr Thr Thr Tyr
65                  70                  75                  80

Met Glu Leu Ser Ser Leu Arg Ser Glu Asp Thr Ala Val Tyr Phe Cys
                85                  90                  95

Ala Thr Asp Arg Ala Pro Val Arg Arg Ala Phe Asp Ile Trp Gly Gln
            100                 105                 110

Gly Thr Met Val Thr Val Ser Ser Gly Ile Leu Gly Ser Gly Gly Gly
        115                 120                 125

Gly Ser Gly Gly Gly Ser Gly Gly Gly Ser Gln Ser Val Leu
    130                 135                 140

Thr Gln Pro Ala Ser Val Ser Gly Ser Pro Gly Gln Ser Val Thr Ile
145                 150                 155                 160

Ser Cys Thr Gly Thr Ser Ser Asp Ile Gly Ser Tyr Lys Phe Val Ser
                165                 170                 175

Trp Tyr Gln His His Pro Gly Lys Ala Pro Lys Leu Met Ile Tyr Asp
            180                 185                 190

Val Thr Gln Arg Pro Ser Gly Val Pro Tyr Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Cys Ser Tyr Ala Gly Asp Tyr Thr Tyr Ala
225                 230                 235                 240

Leu Phe Gly Gly Gly Thr Gln Leu Thr Val Leu Ser
                245                 250

<210> SEQ ID NO 29
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 29

Val Gln Leu Val Gln Ser Gly Ala Glu Val Lys Lys Pro Gly Ala Ser
1               5                   10                  15
```

```
Val Lys Ile Ser Cys Lys Ala Ser Gly Tyr Thr Pro Gly Thr Tyr Thr
            20                  25                  30

Leu His Trp Met Arg Gln Ala Pro Gly Gln Arg Ile Glu Trp Met Gly
        35                  40                  45

Trp Ile Asn Pro Gly Asn Gly Tyr Thr Lys Tyr Ser Gln Arg Phe Gln
    50                  55                  60

Ala Arg Val Thr Ile Asn Arg Asp Thr Ser Thr Thr Thr Tyr Met
65                  70                  75                  80

Glu Leu Ser Ser Leu Arg Ser Glu Asp Thr Ala Val Tyr Phe Cys Ala
                85                  90                  95

Thr Asp Arg Ala Pro Val Arg Arg Ala Phe Asp Ile Trp Gly Gln Gly
            100                 105                 110

Thr Met Val Thr Val Ser Ser
        115

<210> SEQ ID NO 30
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 30

Gln Ser Val Leu Thr Gln Pro Ala Ser Val Ser Gly Ser Pro Gly Gln
1               5                   10                  15

Ser Val Thr Ile Ser Cys Thr Gly Thr Ser Ser Asp Ile Gly Ser Tyr
            20                  25                  30

Lys Phe Val Ser Trp Tyr Gln His Pro Gly Lys Ala Pro Lys Leu
        35                  40                  45

Met Ile Tyr Asp Val Thr Gln Arg Pro Ser Gly Val Pro Tyr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
                85                  90                  95

Tyr Thr Tyr Ala Leu Phe Gly Gly Gly Thr Gln Leu Thr Val Leu Ser
            100                 105                 110

<210> SEQ ID NO 31
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 31

Gly Tyr Thr Leu Gly Thr Tyr Thr
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 32

Ile Asn Pro Gly Asn Gly Tyr Thr
1               5
```

-continued

```
<210> SEQ ID NO 33
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 33

Ala Thr Asp Arg Ala
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 34

Ser Ser Asp Ile Gly Ser Tyr Lys Phe
1               5

<210> SEQ ID NO 35
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 35

Asp Val Thr
1

<210> SEQ ID NO 36
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 36

Cys Ser Tyr Ala Gly Asp Tyr Thr Tyr Ala Leu
1               5                   10

<210> SEQ ID NO 37
<211> LENGTH: 252
<212> TYPE: PRT
<213> ORGANISM: Artificial Sequence
<220> FEATURE:
<223> OTHER INFORMATION: Synthetic Polypeptide

<400> SEQUENCE: 37

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Leu Gly Thr Tyr
            20                  25                  30

Thr Leu His Trp Met Arg Gln Ala Pro Gly Gln Arg Ile Glu Trp Met
        35                  40                  45

Gly Trp Ile Asn Pro Gly Asn Gly Tyr Thr Lys Tyr Ser Gln Arg Phe
    50                  55                  60

Gln Gly Arg Val Thr Ile Asn Arg Asp Thr Ser Ala Thr Thr Thr Tyr
65                  70                  75                  80

Met Glu Leu Ser Ser Leu Arg Ser Glu Asp Thr Ala Val Tyr Phe Cys
                85                  90                  95
```

Ala Thr Asp Arg Ala Pro Val Arg Arg Ala Phe Asp Ile Trp Gly Gln
            100                 105                 110
Gly Thr Met Val Thr Val Ser Ser Gly Ile Leu Gly Ser Gly Gly
        115                 120                 125
Gly Ser Gly Gly Gly Ser Gly Gly Gly Ser Gln Ser Val Leu
    130                 135                 140
Thr Gln Pro Ala Ser Val Ser Gly Ser Pro Gly Gln Ser Val Thr Ile
145                 150                 155                 160
Ser Cys Thr Gly Thr Ser Ser Asp Ile Gly Ser Tyr Lys Phe Val Ser
                165                 170                 175
Trp Tyr Gln His His Pro Gly Lys Ala Pro Lys Leu Met Ile Tyr Asp
            180                 185                 190
Val Thr Gln Arg Pro Ser Gly Val Pro Tyr Arg Phe Ser Gly Ser Lys
        195                 200                 205
Ser Gly Asn Thr Ala Ser Leu Thr Ile Ser Gly Leu Gln Ala Glu Asp
    210                 215                 220
Glu Ala Asp Tyr Tyr Cys Cys Ser Tyr Ala Gly Asp Tyr Thr Tyr Ala
225                 230                 235                 240
Leu Phe Gly Gly Gly Thr Gln Leu Thr Val Leu Ser
                245                 250

<210> SEQ ID NO 38
<211> LENGTH: 756
<212> TYPE: DNA
<213> ORGANISM: Artificial Sequence
<220> FEATURE:
<223> OTHER INFORMATION: Synthetic Polynucleotide

<400> SEQUENCE: 38
caggtccagc ttgtacagtc tggggctgag gtgaagaagc tggggcctc agtgaagatt      60 tcctgcaagg cttctggata caccctcggt acctacactc tgcactggat gcgccaggcc     120
cccggacaaa ggattgagtg gatgggatgg atcaaccctg caatggttac acaaaaatat     180
tcacagaggc tccagggcag agtcaccatt aatagggaca catccgcgac acaacgtac      240 atggagctga gcagcctgag atctgaagac acggctgtat atttctgtgc cagatagg       300 gctccagttc gtcgtgcttt tgatatctgg ggccaaggga caatggtcac cgtctcttca     360
ggaattctag atccggtgg cggtggcagc ggcggtggtg gttccggagg cggcggttct      420
cagtctgttc tgactcagcc tgcctccgtg tctgggtctc ctggacagtc ggtcaccatc     480
tcctgcactg gcaccagcag tgacattggt tcttataaat ttgtctcctg gtaccaacat     540
caccccggca agcccccaa actcatgatt tatgacgtca ctcagcggcc ctcagggtc       600 ccttatcgct tctctggctc caagtctggc aacacggcct ccctgaccat ctctgggctc     660
caggctgaag atgaggctga ttattactgc tgctcatatg caggcgacta cacttatgct     720
ctattcggag gaggcaccca gctgaccgtc ctctcc                               756

<210> SEQ ID NO 39
<211> LENGTH: 756
<212> TYPE: DNA
<213> ORGANISM: Artificial Sequence
<220> FEATURE:
<223> OTHER INFORMATION: Synthetic Polynucleotide

<400> SEQUENCE: 39
caggtccagc ttgtacagtc tggggctgag gtgaagaagc tggggcctc agtgaagatt      60 ccctgcaagg cttctggata caccctcggt acctacactc tgcactggat gcgccaggcc    120

-continued

```
cccggacaaa ggattgagtg gatgggatgg atcaaccctg gcaatggtta cacaaaatat    180
tcacagaggt tccagggcag agtcaccatt aatagggaca catccgcgac acaacgtac     240 atggagctga gcagcctgag atctgaagac acggctgtat atttctgtgc gacagatagg    300
gctccagttc gtcgtgcttt tgatatctgg ggccaaggga caatggtcac cgtctcttca    360
ggaattctag gatccggtgg cggtggcagc ggcggtggtg gttccggagg cggcggttct    420
cagtctgttc tgactcagcc tgcctccgtg tctgggtctc ctggacagtc ggtcaccatc    480
tcctgcactg gcaccagcag tgacattggt tcttataaat ttgtctcctg gtaccaacat    540
caccccggca aagcccccaa actcatgatt tatgatgtca ctcagcggcc ctcaggggtc    600
ccttatcgct tctctggctc caagtctggc aacacggcct ccctgaccat ctctgggctc    660
caggctgaag atgaggctga ttattactgc tgcttatatg caggcgacta cacttatgct    720
ctattcggag gaggcaccca gctgaccgtc ctctcc                              756
```

<210> SEQ ID NO 40
<211> LENGTH: 756
<212> TYPE: DNA
<213> ORGANISM: Artificial Sequence
<220> FEATURE:
<223> OTHER INFORMATION: Synthetic Polynucleotide

<400> SEQUENCE: 40

```
caggtccagc ttgtacagtc tggggctgag gtgaagaagc ctggggcctc agtgaagatt    60
tcctgcaagg cttctggata caccctcggt acctacactc tgcactggat gcgccaggcc    120
cccggacaaa ggattgagtg gatgggatgg atcaaccctg gcaatggtta cacaaaatat    180
tcacagaggt tccagggcag agtcaccatt aatagggaca catccgcgac acaacgtac    240 atggagctga gcagcctgag atctgaagac acggctgtat atttctgtgc gacagatagg    300
gctccagttc gtcgtgcttt tgatatctgg ggccaaggga caatggtcac cgtctcttca    360
ggaattctag gatccggtgg cggtggcagc ggcggtggtg gttccggagg cggcggttcc    420
cagtctgttc tgactcagcc tgcctccgtg tctgggtctc ctgggcagtc ggtcaccatc    480
tcctgcactg gcaccagcag tgacattggt tcttataaat ttgtctcctg gtaccaacat    540
caccccggca aagcccccaa actcatgatt tatgatgtca ctcagcggcc ctcaggggtc    600
ccttatcgct tctctggctc caagtctggc aacacggctt ccctgaccat ctctgggctc    660
caggctgaag atgaggctga ttattactgc tgctcatatg caggcgacta cacttatgct    720
ctattcggag gaggcaccca gctgaccgtc ctctcc                              756
```

<210> SEQ ID NO 41
<211> LENGTH: 755
<212> TYPE: DNA
<213> ORGANISM: Artificial Sequence
<220> FEATURE:
<223> OTHER INFORMATION: Synthetic Polynucleotide

<400> SEQUENCE: 41

```
aggtccagct tgtacagtct ggggctgagg tgaagaagcc tggggcctca gtgaagattt    60
cctgcaaggc ttctggatac accccggta cctacactct gcactggatg cgccaggccc    120
ccggacaaag gattgagtgg atgggatgga tcaaccctgg caatggttac acaaaatatt    180
cacagaggtt ccaggccaga gtcaccatta atagggacac atccgcgacc acaacgtaca    240
tggagctgag cagcctgaga tctgaagaca cggctgtata tttctgtgcg acagataggg    300
```

-continued

```
ctccagttcg tcgtgctttt gatatctggg gccaagggac aatggtcacc gtctcttcag    360
gaattctagg atccggtggc ggtggcagcg gcggtggtgg ttccggaggc ggcggttctc    420
agtctgttct gactcagcct gcctccgtgt ctgggtctcc tggacagtcg gtcaccatct    480
cctgcactgg caccagcagt gacattggtt cttataaatt tgtctcctgg taccaacatc    540
accccggcaa agcccccaaa ctcatgattt atgatgtcac tcagcggccc tcaggggtcc    600
cttatcgctt ctctggctcc aagtctggca acacggcctc cctgaccatc tctgggctcc    660
aggctgaaga tgaggctgat tattattgct gctcatatgc aggcgactac acttatgctc    720
tattcggagg aggcacccag ctgaccgtcc tctcc                               755

<210> SEQ ID NO 42
<211> LENGTH: 756
<212> TYPE: DNA
<213> ORGANISM: Artificial Sequence
<220> FEATURE:
<223> OTHER INFORMATION: Synthetic Polynucleotide

<400> SEQUENCE: 42
caggtccagc ttgtacagtc tggggctgag gtgaagaagc ctggggcctc agtgaagatt     60
tcctgcaagg cttctggata caccctcggt acctacactc tgcactggat gcgccaggcc    120
cccggacaaa ggattgagtg gatgggatgg atcaaccctg caatggtta cacaaaatat    180 tcacagaggt tccagggcag agtcaccatt aataggaca catccgcgac acaacgtac    240 atggagctga gcagcctgag atctgaagac acggctgtat atttctgtgc gacagatagg    300
gctccagttc gtcgtgctt tgatatctgg ggccaaggga caatggtcac cgtctcttca    360
ggaattctag gatccggtgg cggtggcagc ggcggtggtg gttccggagg cggcggttct    420
cagtctgttc tgactcagcc tgcctccgtg tctgggtctc ctggacagtc ggtcaccatc    480
tcctgcactg gcaccagcag tgacattggt tcttataaat tgtctcctg gtaccaacat    540 caccccggca agcccccaa actcatgatt tatgatgtca ctcagcggcc ctcaggggtc    600
ccttatcgct tctctggctc caagtctggc aacacggcct ccctgaccat ctctgggctc    660
caggctgaag atgaggctga ttattactgc tgctcatatg caggcgacta cacttatgct    720
ctattcggag gaggcaccca gctgaccgtc ctctcc                              756
```

HIGH AFFINITY B7-H6 ANTIBODIES AND ANTIBODY FRAGMENTS

CROSS-REFERENCE TO RELATED APPLICATIONS

This application is a divisional of U.S. patent application Ser. No. 16/092,681, filed Oct. 10, 2018, which is a U.S. Nat'l Phase of Int'l Appl. No. PCT/US2017/027615, filed Apr. 14, 2017, which claims the benefit of U.S. Provisional Appl. No. 62/323,039, filed Apr. 15, 2016, each of which is hereby incorporated by reference in its entirety.

SEQUENCE DISCLOSURE

This application includes as part of its disclosure an electronic sequence listing text file named "114325 2o004002.txt", having a size of 30,549 bytes and created on May 11, 2021, which is hereby incorporated by reference in its entirety.

FEDERALLY SPONSORED RESEARCH

This invention was made with government support under P30 GM103415 awarded by National Institutes of Health. The government has certain rights in the invention.

BACKGROUND

B7 ligands are expressed on the cell surface of many different cell types including antigen presenting cells (APCs). The interaction of B7 ligands with receptor molecules on T cells provides activating signals or inhibitory signals that regulate T cell activation and tolerance. Some inhibitory B7 ligands are also expressed on tumor cells, resulting in suppression of immune responses. Stimulating or attenuating the interactions of B7 ligands and their receptors holds therapeutic potential for autoimmune disorders and cancer. B7 homolog 6 (B7-H6) is a specific ligand for the NK cell-activating receptor NKp30. B7-H6 is expressed on various types of primary human tumors, including leukemia, lymphoma, and gastrointestinal stromal tumors, but it is not constitutively expressed on normal tissues.

SUMMARY

Provided herein are antibodies and antigen-binding antibody fragments that bind specifically to B7 homolog 6 (B7-H6) and, in some embodiments, with a higher affinity relative to previously available antibodies and antigen-binding antibody fragments that bind specifically to B7-H6. Further, the antibodies, and antigen-binding antibody fragments, of the present disclosure bind to an epitope of B7-H6 that is different from the epitopes bound by previously available antibodies that bind specifically to B7-H6. It should be understood that, unless otherwise indicated, the term "antibody" encompasses antigen-binding antibody fragments. Thus, if an embodiment encompasses antibodies having a particular property, it should be understood that same embodiment also encompasses an antigen-binding antibody fragment having the same particular property.

Examples of scFv molecules that bind specifically to B7-H6 are provided in FIG. 2 and Table 2.

scFv g2.5-9 is characterized by SEQ ID NO: 1-9, wherein SEQ ID NO: 1 is the complete scFv g2.5-9 amino acid sequence (including the heavy chain and light chain), SEQ ID NO: 2 is the complete scFv g2.5-9 heavy chain sequence, SEQ ID NO: 3 is the complete scFv g2.5-9 light chain sequence, SEQ ID NO: 4 is the CDR1 sequence of the scFv g2.5-9 heavy chain, SEQ ID NO: 5 is the CDR2 sequence of the scFv g2.5-9 heavy chain, SEQ ID NO: 6 is the CDR3 sequence of the scFv g2.5-9 heavy chain, SEQ ID NO: 7 is the CDR1 sequence of the scFv g2.5-9 light chain, SEQ ID NO: 8 is the CDR2 sequence of the scFv g2.5-9 light chain, and SEQ ID NO: 9 is the CDR3 sequence of the scFv g2.5-9 light chain.

scFv g2.5-6 is characterized by SEQ ID NO: 10-18, wherein SEQ ID NO: 10 is the complete scFv g2.5-6 amino acid sequence (including the heavy chain and light chain), SEQ ID NO: 11 is the complete scFv g2.5-6 heavy chain sequence, SEQ ID NO: 12 is the complete scFv g2.5-6 light chain sequence, SEQ ID NO: 13 is the CDR1 sequence of the scFv g2.5-6 heavy chain, SEQ ID NO: 14 is the CDR2 sequence of the scFv g2.5-6 heavy chain, SEQ ID NO: 15 is the CDR3 sequence of the scFv g2.5-6 heavy chain, SEQ ID NO: 16 is the CDR1 sequence of the scFv g2.5-6 light chain, SEQ ID NO: 17 is the CDR2 sequence of the scFv g2.5-6 light chain, and SEQ ID NO: 18 is the CDR3 sequence of the scFv g2.5-6 light chain.

scFv g2.5-3 is characterized by SEQ ID NO: 19-27, wherein SEQ ID NO: 19 is the complete scFv g2.5-3 amino acid sequence (including the heavy chain and light chain), SEQ ID NO: 20 is the complete scFv g2.5-3 heavy chain sequence, SEQ ID NO: 21 is the complete scFv g2.5-3 light chain sequence, SEQ ID NO: 22 is the CDR1 sequence of the scFv g2.5-3 heavy chain, SEQ ID NO: 23 is the CDR2 sequence of the scFv g2.5-3 heavy chain, SEQ ID NO: 24 is the CDR3 sequence of the scFv g2.5-3 heavy chain, SEQ ID NO: 25 is the CDR1 sequence of the scFv g2.5-3 light chain, SEQ ID NO: 26 is the CDR2 sequence of the scFv g2.5-3 light chain, and SEQ ID NO: 27 is the CDR3 sequence of the scFv g2.5-3 light chain.

scFv g2.5-1 is characterized by SEQ ID NO: 28-36, wherein SEQ ID NO: 28 is the complete scFv g2.5-1 amino acid sequence (including the heavy chain and light chain), SEQ ID NO: 29 is the complete scFv g2.5-1 heavy chain sequence, SEQ ID NO: 30 is the complete scFv g2.5-1 light chain sequence, SEQ ID NO: 31 is the CDR1 sequence of the scFv g2.5-1 heavy chain, SEQ ID NO: 32 is the CDR2 sequence of the scFv g2.5-1 heavy chain, SEQ ID NO: 33 is the CDR3 sequence of the scFv g2.5-1 heavy chain, SEQ ID NO: 34 is the CDR1 sequence of the scFv g2.5-1 light chain, SEQ ID NO: 35 is the CDR2 sequence of the scFv g2.5-1 light chain, and SEQ ID NO: 36 is the CDR3 sequence of the scFv g2.5-1 light chain.

Thus, in some embodiments, an antibody, or antigen-binding antibody fragment, binds specifically to B7-H6 and comprises (a) a heavy chain variable region comprising (i) a CDR1 of SEQ ID NO: 4, (ii) a CDR2 of SEQ ID NO: 5, and (iii) a CDR3 of SEQ ID NO: 6, and (b) a light chain variable region comprising (i) a CDR1 of SEQ ID NO: 7, (ii) a CDR2 of SEQ ID NO: 8, and (iii) a CDR3 of SEQ ID NO: 9. In some embodiments, an antibody comprises a heavy chain variable domain of SEQ ID NO: 2. In some embodiments, an antibody comprises a light chain variable domain of SEQ ID NO: 3.

In some embodiments, an antibody, or antigen-binding antibody fragment, binds specifically to B7-H6 and comprises (a) a heavy chain variable region comprising (i) a CDR1 of SEQ ID NO: 13, (ii) a CDR2 of SEQ ID NO: 14, and (iii) a CDR3 of SEQ ID NO: 15, and (b) a light chain variable region comprising (i) a CDR1 of SEQ ID NO: 16, (ii) a CDR2 of SEQ ID NO: 17, and (iii) a CDR3 of SEQ ID NO: 18. In some embodiments, an antibody comprises a heavy chain variable domain of SEQ ID NO: 11. In some embodiments, an antibody comprises a light chain variable domain of SEQ ID NO: 12.

In some embodiments, an antibody, or antigen-binding antibody fragment, binds specifically to B7-H6 and comprises (a) a heavy chain variable region comprising (i) a CDR1 of SEQ ID NO: 22, (ii) a CDR2 of SEQ ID NO: 23, and (iii) a CDR3 of SEQ ID NO: 24, and (b) a light chain variable region comprising (i) a CDR1 of SEQ ID NO: 25, (ii) a CDR2 of SEQ ID NO: 26, and (iii) a CDR3 of SEQ ID NO: 27. In some embodiments, an antibody comprises a heavy chain variable domain of SEQ ID NO: 20. In some embodiments, an antibody comprises a light chain variable domain of SEQ ID NO: 21.

In some embodiments, an antibody, or antigen-binding antibody fragment, binds specifically to B7-H6 and comprises (a) a heavy chain variable region comprising (i) a CDR1 of SEQ ID NO: 31, (ii) a CDR2 of SEQ ID NO: 32, and (iii) a CDR3 of SEQ ID NO: 33, and (b) a light chain variable region comprising (i) a CDR1 of SEQ ID NO: 34, (ii) a CDR2 of SEQ ID NO: 35, and (iii) a CDR3 of SEQ ID NO: 36. In some embodiments, an antibody comprises a heavy chain variable domain of SEQ ID NO: 29. In some embodiments, an antibody comprises a light chain variable domain of SEQ ID NO: 30.

An antibody, or antigen-binding antibody fragment, in some embodiments, has a heavy chain variable region that includes an amino acid sequence identical to (the same as) SEQ ID NO: 2, 11, 20 or 29. In other embodiments, an antibody, or antigen-binding antibody fragment, has a heavy chain variable region that includes an amino acid sequence that is at least 90% identical to SEQ ID NO: 2, 11, 20 or 29. For example, a heavy chain variable region that shares 90% identity with SEQ ID NO: 2, 11, 20 or 29 may include a (at least one) mutation in a (at least one) framework region in SEQ ID NO: 2, 11, 20 or 29. The framework regions are the regions of the heavy chain (or light chain) that do not correspond to the CDR regions.

Thus, in some embodiments, an antibody, or antigen-binding antibody fragment, comprises (a) a heavy chain variable region comprising an amino acid sequence that is (i) identical to (100% identical to) SEQ ID NO: 2, 11, 20 or 29, or (ii) at least 90% (e.g., at least 91%, 92%, 93%, 94%, 95%, 96%, 97%, 98%, or 99%) identical to SEQ ID NO: 2, 11, 20 or 29 and consists of at least one mutation in at least one framework region in SEQ ID NO: 2, 11, 20 or 29, respectively, and (b) a light chain variable region comprising an amino acid sequence that is (i) identical to SEQ ID NO: 3, 12, 21 or 30, or (ii) at least 90% (e.g., at least 91%, 92%, 93%, 94%, 95%, 96%, 97%, 98%, or 99%) identical to SEQ ID NO: 33, 12, 21 or 30 and consists of at least one mutation in at least one framework region in SEQ ID NO: 3, 12, 21 or 30, respectively. In some embodiments, (a) the heavy chain variable region comprises an amino acid sequence that is at least 95% (e.g., at least 96%, 97%, 98%, or 99%) identical to SEQ ID NO: 2, 11, 20 or 29, and (b) the light chain variable region comprises an amino acid sequence that is at least 95% (e.g., at least 96%, 97%, 98%, or 99%) identical to SEQ ID NO: 3, 12, 21 or 30. In some embodiments, (a) the heavy chain variable region comprises an amino acid sequence (i) identical to SEQ ID NO: 2 or (ii) at least 90% (e.g., at least 91%, 92%, 93%, 94%, 95%, 96%, 97%, 98%, or 99%) identical to SEQ ID NO: 2 and consists of at least one mutation in at least one framework region in SEQ ID NO: 2, and (b) the light chain variable region comprises an amino acid sequence (i) identical to SEQ ID NO: 3, or (ii) at least 90% (e.g., at least 91%, 92%, 93%, 94%, 95%, 96%, 97%, 98%, or 99%) identical to SEQ ID NO: 3 and consists of at least one mutation in at least one framework region in SEQ ID NO: 3. In some embodiments, (a) the heavy chain variable region comprises an amino acid sequence identical to SEQ ID NO: 2, and (b) the light chain variable region comprises an amino acid sequence identical to SEQ ID NO: 3. In some embodiments, (a) the heavy chain variable region comprises an amino acid sequence that is at least 95% (e.g., at least 96%, 97%, 98%, or 99%) identical to SEQ ID NO: 2, and (b) the light chain variable region comprises an amino acid sequence that is at least 95% (e.g., at least 96%, 97%, 98%, or 99%) identical to SEQ ID NO: 3.

In some embodiments, (a) the heavy chain variable region comprises an amino acid sequence (i) identical to SEQ ID NO: 11 or (ii) at least 90% (e.g., at least 91%, 92%, 93%, 94%, 95%, 96%, 97%, 98%, or 99%) identical to SEQ ID NO: 11 and consists of at least one mutation in at least one framework region in SEQ ID NO: 11, and (b) the light chain variable region comprises an amino acid sequence (i) identical to SEQ ID NO: 12, or (ii) at least 90% (e.g., at least 91%, 92%, 93%, 94%, 95%, 96%, 97%, 98%, or 99%) identical to SEQ ID NO: 12 and consists of at least one mutation in at least one framework region in SEQ ID NO: 12. In some embodiments, (a) the heavy chain variable region comprises an amino acid sequence identical to SEQ ID NO: 11, and (b) the light chain variable region comprises an amino acid sequence identical to SEQ ID NO: 12. In some embodiments, (a) the heavy chain variable region comprises an amino acid sequence that is at least 95% (e.g., at least 96%, 97%, 98%, or 99%) identical to SEQ ID NO: 11, and (b) the light chain variable region comprises an amino acid sequence that is at least 95% (e.g., at least 96%, 97%, 98%, or 99%) identical to SEQ ID NO: 12.

In some embodiments, (a) the heavy chain variable region comprises an amino acid sequence (i) identical to SEQ ID NO: 20 or (ii) at least 90% (e.g., at least 91%, 92%, 93%, 94%, 95%, 96%, 97%, 98%, or 99%) identical to SEQ ID NO: 20 and consists of at least one mutation in at least one framework region in SEQ ID NO: 20, and (b) the light chain variable region comprises an amino acid sequence (i) identical to SEQ ID NO: 21, or (ii) at least 90% (e.g., at least 91%, 92%, 93%, 94%, 95%, 96%, 97%, 98%, or 99%) identical to SEQ ID NO: 21 and consists of at least one mutation in at least one framework region in SEQ ID NO: 21. In some embodiments, (a) the heavy chain variable region comprises an amino acid sequence identical to SEQ ID NO: 20, and (b) the light chain variable region comprises an amino acid sequence identical to SEQ ID NO: 21. In some embodiments, (a) the heavy chain variable region comprises an amino acid sequence that is at least 95% (e.g., at least 96%, 97%, 98%, or 99%) identical to SEQ ID NO: 20, and (b) the light chain variable region comprises an amino acid sequence that is at least 95% (e.g., at least 96%, 97%, 98%, or 99%) identical to SEQ ID NO: 21.

In some embodiments, (a) the heavy chain variable region comprises an amino acid sequence (i) identical to SEQ ID NO: 29 or (ii) at least 90% (e.g., at least 91%, 92%, 93%, 94%, 95%, 96%, 97%, 98%, or 99%) identical to SEQ ID NO: 29 and consists of at least one mutation in at least one framework region in SEQ ID NO: 29, and (b) the light chain variable region comprises an amino acid sequence (i) identical to SEQ ID NO: 30, or (ii) at least 90% (e.g., at least 91%, 92%, 93%, 94%, 95%, 96%, 97%, 98%, or 99%) identical to SEQ ID NO: 30 and consists of at least one mutation in at least one framework region in SEQ ID NO:

30. In some embodiments, (a) the heavy chain variable region comprises an amino acid sequence identical to SEQ ID NO: 29, and (b) the light chain variable region comprises an amino acid sequence identical to SEQ ID NO: 30. In some embodiments, (a) the heavy chain variable region comprises an amino acid sequence that is at least 95% (e.g., at least 96%, 97%, 98%, or 99%) identical to SEQ ID NO: 29, and (b) the light chain variable region comprises an amino acid sequence that is at least 95% (e.g., at least 96%, 97%, 98%, or 99%) identical to SEQ ID NO: 30.

Also provided herein are recombinant T cells comprising an antibody or antigen-binding antibody fragment of the present disclosure that binds specifically to B7-H6.

Further provided herein are pharmaceutical compositions comprising an antibody or antigen-binding antibody fragment of the present disclosure that binds specifically to B7-H6.

Also provided herein, in some embodiments, kits comprising an antibody or antigen-binding antibody fragment of the present disclosure that specifically binds to B7-H6.

In some embodiments, provided herein are chimeric antigen receptors comprising (a) an antigen-binding antibody fragment of the present disclosure that binds specifically to B7-H6, (b) a transmembrane domain, and (c) an intracellular signaling domain. In some embodiments, a recombinant T cell comprises a chimeric antigen receptor comprising an antigen-binding antibody fragment of the present disclosure that binds specifically to B7-H6, (b) a transmembrane domain, and (c) an intracellular T-cell receptor signaling domain.

Also provided herein are bi-specific T-cell engagers comprising (a) an antigen-binding antibody fragment of the present disclosure that binds specifically to B7-H6, and (b) an antigen binding domain that binds to a T-cell antigen.

Some embodiments of the present disclosure provide methods for killing or inhibiting the growth of cells expressing B7 homolog 6 in a subject comprising administering an effective amount of an antibody or antigen-binding antibody fragment of the present disclosure that binds specifically to B7-H6, thereby killing or inhibiting the growth of cells expressing B7-H6 in the subject.

Some embodiments of the present disclosure provide methods of reducing growth of cancerous cells that express B7 homolog 6 in a subject, the method comprising administering to a subject having cancerous cells that express B7 homolog 6 an effective amount of an antibody or antigen-binding antibody fragment of the present disclosure that binds specifically to B7-H6.

BRIEF DESCRIPTION OF THE DRAWINGS

FIG. 3A shows cell-binding curves of a representative isolate, g2.5-11 scFv-Fc (equivalent to g2.5-3 at the amino acid level), to antigen-expressing RMA-B7H6 and negative control RMA cells.

FIGS. 4A and 4B show results from competitive assays for binding of g2.5-11 scFV-Fc and murine TZ47 to RMA-B7H6 cells. FIG. 4A shows staining for g2.5-11 and FIG. 4B shows staining for TZ47 (measured by FITC).

DESCRIPTION

Provided herein are antibodies and antigen-binding antibody fragments that bind specifically to B7 homolog 6 (B7-H6), which is expressed on various types of primary human tumors, including leukemia, lymphoma, and gastrointestinal stromal tumors. The antigen-binding antibody fragments, for example, were shown to bind to B7-H6 with an affinity that is greater than that of previously available anti-B7-H6 antibodies and were shown to bind to an epitope that is different from that bound by previously available anti-B7-H6 antibodies. The antigen-binding antibody fragments, as provided herein, in some embodiments, are used to produce chimeric antigen receptors and bi specific T cell engagers (BiTEs) for use, for example, in the treatment of cancer and autoimmune disorders.

Figure 2:
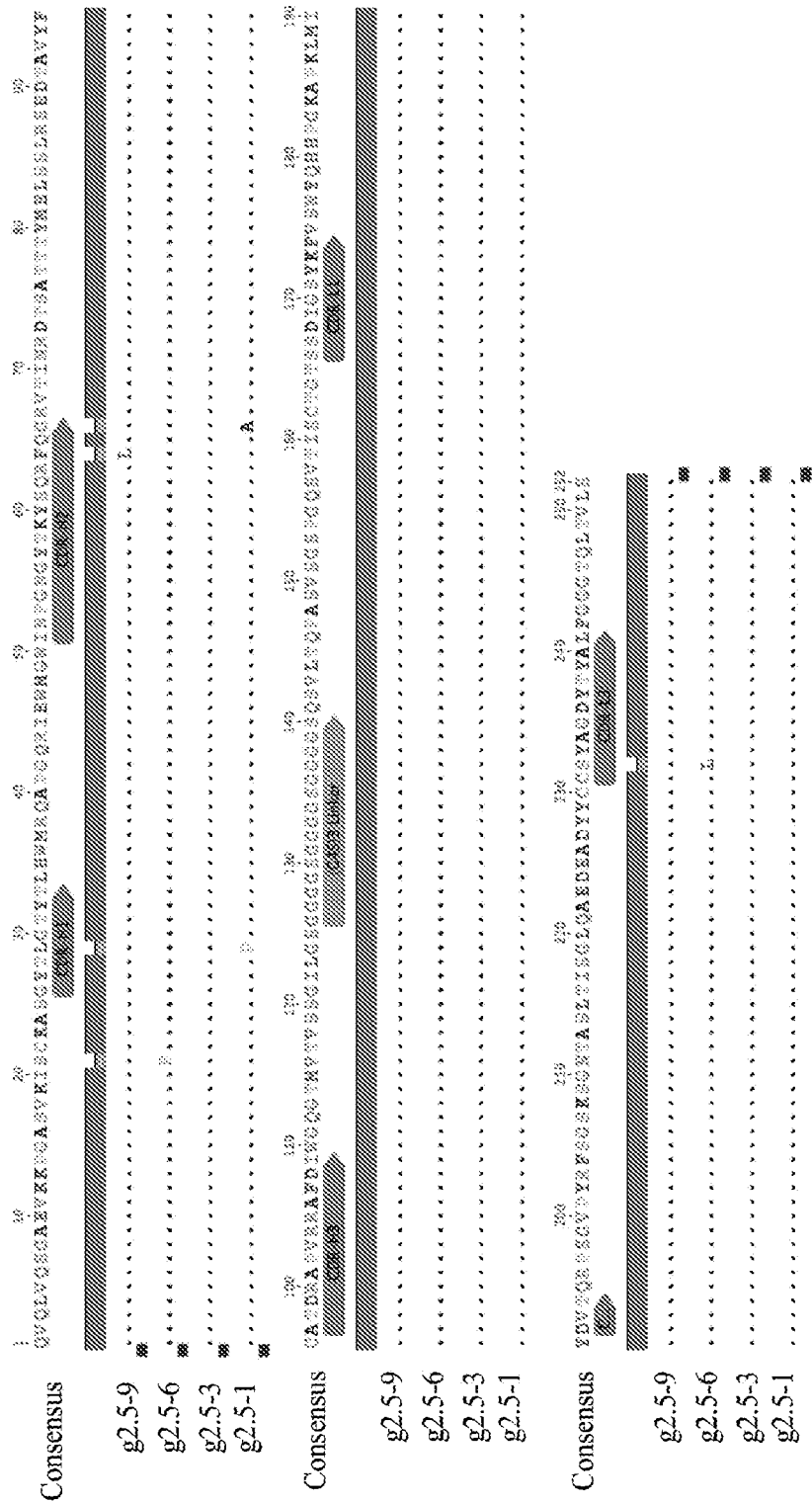
FIG. 2 shows isolated B7H6 scFv sequence alignments. Distinct isolated clones g2.5-9 scFv (SEQ ID NO: 1), g2.5-6 scFv (SEQ ID NO: 10), g2.5-3 scFv (SEQ ID NO: 19), and g2.5-1 scFv (SEQ ID NO: 28) are shown compared to the consensus sequence (SEQ ID NO: 37). CDRs as defined by VBASE2 are annotated.

Examples of scFv antibody fragments that bind specifically to B7-H6 are provided in FIG. 2 and Table 2. FIG. 2 shows an amino acid alignment of four different scFV antibody fragments relative to a consensus sequence (SEQ ID NO: 37). B7-H6-binding variants of the scFV antibody fragments of FIG. 2 and Table 2 are encompassed by the present disclosure.

An antibody or an antigen-binding domain (e.g., an scFV) that "binds specifically" to B7-H6 or other target or epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antigen binding domain (e.g., an scFV) that binds specifically to a first target antigen may or may not bind specifically to a second target antigen. As such, "specific binding" does not necessarily require (although it can include) exclusive binding.

In some embodiments, antibodies and antigen-binding antibody fragments that bind specifically to B7-H6 have a heavy chain amino acid sequence of SEQ ID NO: 2, 11, 20 or 29. In some embodiments, antibodies and antigen-binding antibody fragments that bind specifically to B7-H6 have a heavy chain amino acid sequence that is at least 80% (e.g., at least 85%, 90%, 95%, 96%, 97%, 98%, 99%) identical to SEQ ID NO: 2, 11, 20 or 29. In some embodiments, antibodies and antigen-binding antibody fragments that bind specifically to B7-H6 have a light chain amino acid sequence of SEQ ID NO: 3, 12, 21 or 30. In some embodiments, antibodies and antigen-binding antibody fragments that bind specifically to B7-H6 have a light chain amino acid sequence that is at least 80% (e.g., at least 85%, 90%, 95%, 96%, 97%, 98%, 99%) identical to SEQ ID NO: 3, 12, 21 or 30.

In some embodiments, the heavy chain variable ($V_H$) region of the antibody or antibody fragment has a CDR1 sequence of SEQ ID NO: 4, 13, 22 or 31. In some embodiments, the heavy chain variable ($V_H$) region of the antibody or antibody fragment has a CDR1 sequence that is at least 80% (e.g., at least 85%, 90%, 95%, 96%, 97%, 98%, 99%) identical to SEQ ID NO: 4, 13, 22 or 31. In some embodiments, the heavy chain variable region of the antibody or antibody fragment has a CDR2 sequence of SEQ ID NO: 5, 14, 23 or 32. In some embodiments, the heavy chain variable region of the antibody or antibody fragment has a CDR2 sequence that is at least 80% (e.g., at least 85%, 90%, 95%, 96%, 97%, 98%, 99%) identical to SEQ ID NO: 5, 14, 23 or 32. In some embodiments, the heavy chain variable region of the antibody or antibody fragment has a CDR3 sequence of SEQ ID NO: 6, 15, 24 or 33. In some embodiments, the heavy chain variable region of the antibody or antibody fragment has a CDR3 sequence that is at least 80% (e.g., at least 85%, 90%, 95%, 96%, 97%, 98%, 99%) identical to SEQ ID NO: 6, 15, 24 or 33.

In some embodiments, the light chain variable ($V_L$) region of the antibody or antibody fragment has a CDR1 sequence of SEQ ID NO: 7, 16, 25 or 34. In some embodiments, the light chain variable ($V_L$) region of the antibody or antibody fragment has a CDR1 sequence that is at least 80% (e.g., at least 85%, 90%, 95%, 96%, 97%, 98%, 99%) identical to SEQ ID NO: 7, 16, 25 or 34. In some embodiments, the light chain variable ($V_L$) region of the antibody or antibody fragment has a CDR2 sequence of SEQ ID NO: 8, 17, 26 or 35. In some embodiments, the light chain variable ($V_L$) region of the antibody or antibody fragment has a CDR2 sequence that is at least 80% (e.g., at least 85%, 90%, 95%, 96%, 97%, 98%, 99%) identical to SEQ ID NO: 8, 17, 26 or 35. In some embodiments, the light chain variable ($V_L$) region of the antibody or antibody fragment has a CDR3 sequence of SEQ ID NO: 9, 18, 27 or 36. In some embodiments, the light chain variable ($V_L$) region of the antibody or antibody fragment has a CDR3 sequence that is at least 80% (e.g., at least 85%, 90%, 95%, 96%, 97%, 98%, 99%) identical to SEQ ID NO: 9, 18, 27 or 36.

Also provided herein are functional variants of the scFv antibody fragments provided in FIG. 2 and Table 2. Thus, in some embodiments, a heavy chain variable region of an antibody or antibody fragment is at least 80% (e.g., 85%, 90%, 95%, 96%, 97%, 98%, or 99%) identical to SEQ ID NO: 2, 11, 20 or 29. In some embodiments, a heavy chain variable region of an antibody or antibody fragment is at least 80% (e.g., 85%, 90%, 95%, 96%, 97%, 98%, or 99%) identical to SEQ ID NO: 2, 11, 20 or 29 and consists of at least one mutation in at least one framework region in SEQ ID NO: 2, 11, 20 or 29, respectively.

In some embodiments, a light chain variable region of an antibody or antibody fragment is at least 80% (e.g., 85%, 90%, 95%, 96%, 97%, 98%, or 99%) identical to SEQ ID NO: 33, 12, 21 or 30. In some embodiments, a light chain variable region of an antibody or antibody fragment is at least 80% (e.g., 85%, 90%, 95%, 96%, 97%, 98%, or 99%) identical to SEQ ID NO: 33, 12, 21 or 30 and consists of at least one mutation in at least one framework region in SEQ ID NO: 3, 12, 21 or 30, respectively.

Functional variants are capable of binding to a B7-H6 molecule, particularly a human B7-H6 molecule. In some embodiments, the variants possess similar antigen-binding affinity relative to the B7-H6 scFvs provided in FIG. 2 and Table 2 (e.g., the $K_D$ between the variant and B7H6 is 100 pM to 1 µM).

In some embodiments, the functional variants described above contains one or more mutations (e.g., conservative substitutions) in the framework region (FR) of the $V_H$ relative to SEQ ID NO: 2, 11, 20 or 29. In some embodiments, the functional variants described above contains one or more mutations (e.g., conservative substitutions) in the FR $V_L$ relative to SEQ ID NO: 33, 12, 21 or 30. These mutations, in some embodiments, do not occur at residues which are predicted to interact with one or more of the CDRs. Mutations within the FR are unlikely to affect the antigen-binding activity of an antibody or antigen-binding antibody fragment. In some embodiments, the functional variants described herein contain at least one (e.g., 1, 2 or 3) mutations within at least one of the CDR regions. These functional variants, in some embodiments, retain the same regions/residues responsible for antigen-binding as the parent, such as the same specificity-determining residues inside the CDRs.

The "percent identity" of two amino acid sequences can be determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed, for example, with the XBLAST program, score=50, wordlength=3 to obtain amino acid sequences homologous to the protein molecules of interest. Where gaps exist between two sequences, Gapped BLAST can be utilized, for example, as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used, in some embodiments.

Provided herein are full length antibodies and antigen-binding antibody fragments (including single-chain antibodies). In some embodiments, an antibody fragment that specifically binds to B7-H6 is an scFV antibody fragment. Other examples of antibody fragments include, but are not limited to, F(ab)2, Fv, scFv, F(ab')$_2$, F(ab), VL, VH, dsFv, Fv, scFv-Fc, (scFv)$_2$, diabodies and bivalent antibodies.

An antibody (or an antigen-binding antibody fragment) may be, for example, polyclonal, monoclonal, recombinant, chimeric or humanized. In some embodiments, an antibody is an IgA, IgD, IgE, IgG, or IgM isotype. Other isotypes are encompassed by the present disclosure. In some embodiments, an antibody that binds specifically to B7-H6 is an IgA, such as IgA1 or IgA2, or is am IgG, such as IgG1, IgG2, IgG3, IgG4, or synthetic IgG. In some embodiments, an antibody (or an antigen-binding fragment of the antibody) is a synthetic antibody, such as a non-depleting IgG antibody, T-body, or other Fc or Fab variant of antibody.

In some embodiments, an antibody is an isolated antibody.

Antibodies, and antigen-binding antibody fragments, in some embodiments, have an affinity for B7-H6 of 100 pM to 1 µM. In some embodiments, antibodies have an affinity for B7-H6 of 100 pM to 1 µM. For example, antibodies may have an affinity for B7-H6 of 100-200 pM, 100-300 pM, 100-400 pM, 100-500 pM, 100-600 pM, 100-700 pM, 100-800 pM or 100-900 pM. In some embodiments, antibodies have an affinity for B7-H6 of 1-10 nM, 1-100 nM, or 1-1000 nM (1 µM). For example, antibodies may have an affinity for B7-H6 of 1-5 nM, 1-25 nM, 1-50 nM, 1-75 nM, 1-150 nM, 1-200 nM, 1-300 nM, 1-400 nM, 1-500 nM, 1-600 nM, 1-700 nM, 1-800 nM or 1-900 nM.

In some embodiments, antibodies have an affinity for B7-H6 of 10 nM to 50 nM (e.g., 10 nM, 15 nM, 20 nM, 25 nM, 30 nM, 35 nM, 40 nM, 45 nM, or 50 nM). In some embodiments, antibodies have an affinity for B7-H6 of at least 10 nM. For example, antibodies may have an affinity for B7-H6 of at least 15 nM, at least 20 nM, at least 30 nM, at least 40 nM, at least 45 nM, or at least 50 nM. In some embodiments, antibodies have an affinity for B7-H6 of 15 nM to 50 nM, 20 nM to 50 nM, or 30 nM to 50 nM. In some embodiments, antibodies have an affinity for B7-H6 of less than 10 nM.

Affinity can be measured using known techniques. The affinity of an antibody can be determined by measuring the $K_D$ of the antibody. The $K_D$ is the equilibrium dissociation constant (a ratio of $k_{off}/k_{on}$) between an antibody and its antigen, where $K_{off}$ is the antibody dissociation rate (the rate at which an antibody dissociates from its antigen), and $K_{on}$ is the antibody association rate (the rate at which an antibody binds to its antigen). $K_D$ and affinity are inversely related. The $K_D$ value relates to the concentration of antibody—the lower the $K_D$ value (lower concentration), the higher the affinity of the antibody.

Antibodies, and antigen-binding antibody fragments, in some embodiments, have an avidity for B7-H6 of 1 µM to 10 nM. In some embodiments, antibodies have an avidity for B7-H6 of 10 µM or less. For example, antibodies may have an avidity for B7-H6 of 5 µM or less, 2 µM or less, 1 µM or less, 500 nM or less, 400 nM or less, 300 nM or less, or 200 nM or less. n some embodiments, antibodies have an avidity for B7-H6 of 100 nM or less, 75 nM or less, 50 nM or less, 25 nM or less, 10 nM or less, or 5 nM or less. Avidity refers to the accumulated strength of multiple affinities of individual antibody-antigen binding interactions (compare to affinity, which describes the strength of a single interaction). Avidity can be measured using techniques, such as an enzyme-linked immunosorbent assay (ELISA) or a BIA-CORE® detection system.

Antibodies, and antigen-binding antibody fragments, may be produced used a eukaryotic expression system or a non-eukaryotic expression system. In some embodiments, an antibody is produced using a mammalian expression system. In some embodiments, the antibody (or antibody fragment) is encoded by a DNA sequence selected from any one of SEQ ID NO: 38-41. In some embodiments, an antibody is produced using a bacterial expression system. For example, a bacterial expression system may be used to produce antibody fragments, such as F(ab)$_2$, Fv, scFv, F(ab')$_2$, F(ab), VL, VH, dsFv, Fv, scFv-Fc, (scFv)$_2$ and diabodies. Techniques for altering DNA coding sequences to produce such fragments are known.

An antibody, or antigen-binding antibody fragment, in some embodiments, is conjugated to a synthetic molecule. In some embodiments, a synthetic molecule is a molecule that targets (recognizes and binds to) a particular cell or cell type, such as a tumor cell (e.g., a cancerous tumor cell) or a metastatic cell.

In some embodiments, a synthetic molecule is a therapeutic molecule, such as a cytotoxic molecule (e.g., a protein toxin obtained from a plant, fungus or bacterium), a cytostatic molecule, an anti-angiogenic molecule or a radioisotope.

Examples, of therapeutic molecules include, but are not limited to, maytansinoids (e.g., maytansinol or DM1 maytansinoid), taxanes, calicheamicin, vincristine and prednisone. A therapeutic molecule, in some embodiments, is: an antimetabolite (e.g., an antifolate such as methotrexate, a fluoropyrimidine such as 5-fluorouracil, cytosine arabinoside, or an analogue of purine or adenosine); an intercalating agent (e.g., an anthracycline such as doxorubicin, daunomycin, epirubicin, idarubicin, mitomycin-C, dactinomycin, or mithramycin); a platinum derivative (e.g., cisplatin or carboplatin); an alkylating agent (e.g., nitrogen mustard, melphalan, chlorambucil, busulphan, cyclophosphamide, ifosfamide nitrosoureas or thiotepa); an antimitotic agent (e.g., a vinca alkaloid, such as vincristine, or taxoid, such as paclitaxel or docetaxel); a topoisomerase inhibitor (e.g., etoposide and teniposide, amsacrine, topotecan); a cell cycle inhibitor (e.g., a flavopyridol); or a microbtubule agent (e.g., an epothilone, discodermolide analog or eleutherobin analog). In some embodiments, a therapeutic molecule is a proteosome inhibitor or a topoisomerase inhibitor, such as bortezomib, amsacrine, etoposide, etoposide phosphate, teniposide or doxorubicin.

Examples of cytotoxic molecules include, but are not limited to, auristatins, maytansines, calicheamicins, duocarymycins, PBD dimers and alpha-amanitin. Examples of cytotoxic/immunosuppressive molecules include, but are not limited to, cyclophosphamide (e.g., Cytoxan), azathioprine (e.g., Imuran) and methotrexate.

Examples of anti-angiogenic agents include, but are not limited to, linomide, bevacuzimab, angiostatin and razoxane. The synthetic molecule can be another antibody such as rituximab or bevacuzimab.

Examples of therapeutic radioisotopes include, but are not limited to, yttrium (90Y), lutetium (177Lu), actinium (225Ac)) bismuth (212Bi praseodymium, astatine (211At) rhenium (186Re), bismuth (212Bi or 213Bi) and rhodium (188Rh).

In some embodiments, a synthetic molecule is a fusion protein produced, for example, by conventional recombinant protein expression systems and methods.

In some embodiments, a synthetic molecule is a label. Labels can be useful in diagnostic applications and can include, for example, contrast agents. Examples of contrast agents include, but are not limited to, radioisotope labels such as iodine (131I or 125I), indium In), technetium (99Tc), phosphorus (32P), carbon (14C), tritium (3H) and other radioisotopes (e.g., a radioactive ion) listed above; radiopaque molecule, magnetic resonance imaging (MRI) molecule, ultrasound imaging molecule, and any other contrast molecule suitable for detection by a device that images an animal body. In some embodiments, a synthetic molecule is a fluorescent label, a biologically active enzyme label, a luminescent label, or a chromophore label.

In some embodiments, a synthetic molecule is a magnetic nanoparticle, a controlled release polymer nanoparticle or a lipid composition. Examples of magnetic nanoparticles include, but are not limited to, iron (e.g., $Fe_3O_4$ or $Fe_2O_4$), cobalt, zinc, cadmium, nickel, gadolinium, chromium, copper, manganese, terbium, europium, gold, silver, platinum, and alloys thereof. Controlled release polymer nanoparticles can be produced using conventional methods, for example, from biodegradable or nonbiodegradable polymers, e.g., poly(lactic acid), derivatives of poly(lactic acid), PEGylated poly(lactic acid), poly(lactic-co-glycolic acid), derivatives of poly(lactic-co-glycolic acid), PEGylated poly(lactic-co-glycolic acid), a polyanhydride, poly(ortho esters), derivatives of poly(ortho esters), PEGylated poly(ortho esters), poly(caprolactone), derivatives of poly(caprolactone), PEGylated poly(caprolactone), poly(acrylic acid), derivatives of poly(acrylic acid), poly(urethane), derivatives of poly(urethane), or combinations thereof). Similarly, lipid compositions (e.g., liposomes, solid lipid nanoparticles and the like) can be produced using conventional methods.

An anti-B7-H6 antibody, or antigen-binding antibody fragment, can be conjugated to a synthetic molecule using any type of suitable conjugation method. Recombinant engineering and incorporated selenocysteine (e.g., as described in WO 2008/122039) can be used to conjugate a synthetic molecule, for example. Other methods of conjugation include, but are not limited to covalent coupling to native or engineered lysine side-chain amines or cysteine side-chain thiols. See, e.g., Wu, et al. (2005) *Nat. Biotechnol.* 23:1137-1146.

Also provided herein are chimeric antigen receptors (CARs). A T cell that expressed a CAR is referred to as a "CAR T cell." A CAR T cell receptor, in some embodiments, comprises a signaling domain of the T-cell receptor (TcR) complex and a B7-H6-recognizing domain (e.g., a single chain fragment (scFv) of FIG. 2 or Table 2) (Enblad et al., *Human Gene Therapy.* 2015; 26(8):498-505).

There are four generations of CARs, each of which contains different components. First generation CARs join an antibody-derived scFv to the CD3zeta or z) intracellular signaling domain of the T-cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TeR CD3-ζ chain. Third-generation costimulatory domains may include, e.g., a combination of CD3z, CD27, CD28, 4-1BB, ICOS, DAP-10 or OX40. CARs, in some embodiments, contain an ectodomain (e.g., CD3ζ), commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., *Blood.* 2015; 125(26):4017-4023; Kakarla and Gottschalk, *Cancer J.* 2014; 20(2):151-155).

In some embodiments, the chimeric antigen receptor (CAR) is a T-cell redirected for cytokine activity (e.g., TRUCK), also known as a fourth generation CAR. TRUCKs are CAR-redirected T-cells used as vehicles to trigger effector activity of the CAR T cells and in addition produce and release a transgenic cytokine (e.g., IL-12) that accumulates in the targeted tissue, e.g., a tumor tissue that expresses B7-H6. The transgenic cytokine is made constitutively or released upon CAR engagement of the target. TRUCK cells may deposit a variety of therapeutic cytokines at the target site. This may result in therapeutic concentrations at the targeted site and avoid systemic toxicity of these same cytokines.

CARs typically differ in their functional properties. The CD3ζ signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to their specific antigen. The addition of a costimulatory domain in second-generation CARs improved replicative capacity and persistence of modified T-cells. Similar antitumor effects are observed in vitro with CD28 or 4-1 BB CARs, but preclinical in vivo studies suggest that 4-1BB CARs may produce superior proliferation and/or persistence. Clinical trials suggest that both of these second-generation CARs are capable of inducing substantial T-cell proliferation in vivo, but CARs containing the 4-1BB costimulatory domain appear to persist longer. Third generation CARs combine multiple signaling domains (costimulatory) to augment potency. Fourth generation CARs are additionally modified with a constitutive or inducible expression cassette for a transgenic cytokine, which is released by the CAR T-cell to modulate the immune response. See, for example, Enblad et al., *Human Gene Therapy.* 2015; 26(8):498-505; Chmielewski and Hinrich, *Expert Opinion on Biological Therapy.* 2015; 15(8): 1145-1154.

In some embodiments, a chimeric antigen receptor is a first generation CAR. In some embodiments, a chimeric antigen receptor is a second generation CAR. In some embodiments, a chimeric antigen receptor is a third generation CAR. In some embodiments, the chimeric antigen receptor is a fourth generation CAR or a T cell redirected to produce additional cytokines (TRUCK).

A chimeric antigen receptor (CAR) may comprise an extracellular domain comprising a B7-H6 binding domain, a transmembrane domain, and a cytoplasmic domain. In some embodiments, a CAR is fully human. A "spacer" domain or "hinge" domain may be located between an extracellular domain (comprising the antigen binding domain) and a transmembrane domain of a CAR, or between a cytoplasmic domain and a transmembrane domain of the CAR. A "spacer domain" refers to any oligopeptide or polypeptide that functions to link the transmembrane domain to the extracellular domain and/or the cytoplasmic domain in the polypeptide chain. A "hinge domain" refers to any oligopeptide or polypeptide that functions to provide flexibility to the CAR, or domains thereof, or to prevent steric hindrance of the CAR, or domains thereof. In some embodiments, a spacer domain or hinge domain may comprise up to 300 amino acids (e.g., 10 to 100 amino acids, or 5 to 20 amino acids). In some embodiments, one or more spacer domain(s) may be included in other regions of a CAR.

In some embodiments, a CAR comprises an antigen binding domain, such as a single chain Fv (scFv) specific for B7-H6.

In some embodiments, T cells expressing a CAR are genetically modified to recognize multiple targets or antigens, which permits the recognition of unique target or antigen expression patterns on tumor cells. Examples of CARs that can bind multiple targets include: "split signal CARs," which limit complete T cell activation to tumors expressing multiple antigens; "tandem CARs" (TanCARs), which contain ectodomains having two scFvs; and "universal ectodomain CARs," which incorporate avidin or a fluorescein isothiocyanate (FITC)-specific scFv to recognize tumor cells that have been incubated with tagged monoclonal antibodies (blabs).

A CAR is considered "bispecific" if it recognizes two distinct antigens (has two distinct antigen recognition domains). In some embodiments, a bispecific CAR is comprised of two distinct antigen recognition domains present in tandem on a single transgenic receptor (referred to as a TanCAR; see, e.g., Grada Z et al. *Molecular Therapy Nucleic Acids* 2013; 2:e105, incorporated herein by reference).

In some embodiments, a CAR is an antigen-specific inhibitory CAR (iCAR), which may be used, for example, to avoid off-tumor toxicity (Fedorov, V D et al. *Sci. Transl. Med.* published online Dec. 11, 2013, incorporated herein by reference). iCARs contain an antigen-specific inhibitory receptor, for example, to block nonspecific immunosuppression, which may result from extra-tumor target expression. iCARs may be based, for example, on inhibitory molecules CTLA-4 or PD-1. In some embodiments, these iCARS block T cell responses from T cells activated by either their endogenous T cell receptor or an activating CAR. In some embodiments, this inhibiting effect is temporary.

In some embodiments, CARs may be used in adoptive cell transfer, wherein immune cells are removed from a subject and modified so that they express receptors specific to B7-H6. The modified immune cells, which may then recognize and kill the cancer cells, are reintroduced into the subject (Pule, et al., *Cytotherapy.* 2003; 5(3): 211-226; Maude et al., *Blood.* 2015; 125(26): 4017-4023, each of which is incorporated herein by reference).

CARs may be prepared using standard recombinant protein techniques using sequences of CD3-zeta and other costimulatory molecules known in the art. For example, the human CD3-zeta sequence is available under GENBANK accession number NP 932170 (e.g., entry as of Mar. 18, 2016), the human CD28 sequence is available under GENBANK accession number NP 006130 (e.g., entry as of Mar. 18, 2016), the human OX40 sequence is available under GENBANK accession number NP_003318 (e.g., entry as of Mar. 18, 2016), and the human CD19 sequence is available under GENBANK accession number AAA69966 (e.g., entry as of Mar. 18, 2016).

In some embodiments, an antibody, or an antigen-binding antibody fragment, also has specificity for one or more antigens in addition to B7-H6. For example, the antibody may be engineered (e.g., as a bivalent diabody or a conjugated Fab dimer or trimer) to have specificity for B7-H6 and another tumor antigen, for example, an antigen associated with lymphoma, leukemia, melanoma, or sarcoma. In some embodiments, an antibody is engineered to have specificity for B7-H6 and an antigen that promotes activation or targeting of other cells, such as cytotoxic effector cells or T cells. Accordingly, the present disclosure also provides BiTES (bi-specific T-cell engagers) and DARTS (dual affinity retargeting reagents).

A BiTE refers to a single polypeptide chain molecule having two antigen binding domains, one of which binds to a T-cell antigen (e.g., CD3) and the other of which binds to an antigen present on the surface of a target cell (WO 05/061547; Baeuerle, et al. (2008) *Drugs of the Future* 33:137-147; Bargou, et al. (2008) *Science* 321:974-977). BiTE antibodies have been constructed to target various antigens including CD19, EpCAM, Her2/neu, EGFR, CD66e (or CEA, CEACAM5), CD33, EphA2 and MCSP (or HMW-MAA) (Baeuerle, et al. (2009) *Curr. Opin. Mol. Ther.* 11:22-30). Key features of BiTE antibodies that, in their combination, distinguish them from other bispecific antibody constructs include a high potency of redirected lysis with $EC_{50}$ values ranging from 0.1 to 50 pmol/L (2-1,000 pg/mL) (Baeuerle, et al. (2009) supra); strict target cell-dependent activation of T cells (Brischwein, et al. (2007) *J. Immunother.* 30:798-807); and support of serial lysis by activated T cells (activity at low E:T ratios). BiTE antibodies are typically produced as recombinant, glycosylated proteins secreted by higher eukaryotic cell lines. Accordingly, in some embodiments of the present disclosure, an anti-B7-H6 antibody fragment (e.g., a scFv) is a component of a BiTE. In particular embodiments, a BiTE is composed of an anti-B7-H6 antibody fragment and an anti-CD3 antibody fragment fused together by a linker, for example, a (G4S)3 linker.

A DART refers to an immunoglobulin molecule that includes at least two polypeptide chains that associate (especially through a covalent interaction) to form at least two epitope binding sites, which may recognize the same epitope or different epitopes. Each of the polypeptide chains of a DART include an immunoglobulin light chain variable region and an immunoglobulin heavy chain variable region, but these regions do not interact to form an epitope binding site. Rather, the immunoglobulin heavy chain variable region of one (e.g., the first) of the DART polypeptide chains interacts with the immunoglobulin light chain variable region of a different (e.g., the second) DART polypeptide chain to form an epitope binding site. Similarly, the immunoglobulin light chain variable region of one (e.g., the first) of the DART polypeptide chains interacts with the immunoglobulin heavy chain variable region of a different (e.g., the second) DART polypeptide chain to form an epitope binding site. DARTs may be monospecific, bispecific or trispecific, for example, thus they are capable of simultaneously binding one, two or three (or more) different epitopes (which may be of the same or of different antigens). DARTs may additionally be monovalent, bivalent, trivalent, tetravalent, pentavalent or hexavalent, for example, thus are capable of simultaneously bind one, two, three, four, five, six or more molecules. These two features of DARTs (degree of specificity and valency) may be combined, for example to produce bispecific antibodies (capable of binding two epitopes) that are tetravalent (capable of binding four sets of epitopes, for example. Examples of methods of constructing DART molecules is disclosed in WO 2006/113665, WO 2008/157379 and WO 2010/080538. Accordingly, in some embodiments, an anti-B7-H6 antibody fragment is a component of a DART.

The present disclosure further provides eukaryotic or non-eukaryotic cells that are recombinantly engineered to produce an antibody or an antigen-binding antibody fragment that binds specifically to B7-H6. The eukaryotic or non-eukaryotic cells can be used, for example, as an expression system to produce the antibody. In some embodiments, the present disclosure provides B7-H6 targeted immune cells (e.g., T cells or B cells) that are engineered to recombinantly express a B7-H6 specific antibody. For example, a T-cell may be engineered to express an antibody or an antigen-binding antibody fragment (e.g., an scFv, scFv-Fc, $(scFv)_2$) that binds specifically to B7-H6. In some embodiments, the antibody, or an antigen-binding antibody fragment, is linked to a synthetic molecule with the following domains: a spacer domain or hinge domain (e.g., a CD28 or IgG hinge domain), a transmembrane domain (e.g., a transmembrane canonical domain), and an intracellular signaling domain (e.g., a T-cell receptor (TCR) signaling domain or a FcR-gamma intracellular signaling domain), thereby forming a CAR. Examples of intracellular signaling domains that can be included in a CAR include, but are not limited to, CD3zeta, FcR-gamma and Syk-PTK signaling domains as well as the CD28, 4-1BB and CD134 co-signaling domains. Methods for producing T-cells (and other immune cells) expressing a CAR are known. See, e.g., Marcu-Malina, et al. (2009) *Exp. Opin. Biol. Ther.* 9:579-91.

The present disclosure also provides methods of killing, inhibiting the growth of (e.g., proliferation), or inhibiting the activity of cells that express B7-H6 (B7-H6 cells) by contacting the cells with (administering to the cells or to a subject having the cells) an antibody, antigen-binding antibody fragment or fusion protein (e.g., BiTE) that binds specifically to B7-H6. "Inhibiting" B7-H6-positive cell growth or activity can include blocking or reducing growth or activity (e.g., secretion of certain molecules). In some embodiments, the antibody is conjugated (linked to) to a synthetic molecule. In some embodiments, and antibody is conjugated to a cytotoxic molecule (e.g., *Pseudomonas* exotoxin A (PE38)), cytostatic molecule, anti-angiogenic molecule or a radioisotope. Methods can be used to kill or inhibit growth of B7-H6 cells in vitro or in vivo (in a subject, such as a human subject). Thus, also provided herein, in some embodiments, are methods of treating a subject that has, is suspected to have, or is at risk for a condition characterized by increased levels of cellular B7-H6 expression. "Treating" can include curing or reducing the symptoms associated with the particular condition. Thus, treating does not necessarily imply 100% or complete treatment. Rather, there are varying degrees of treatment of which one of ordinary skill in the art recognizes as having a potential benefit or therapeutic effect. Treatment provided by the present disclosure can include the treatment of one or more conditions or symptoms of the disease being treated.

"Increased amounts of cellular B7-H6 expression" is typically relative to a normal (healthy) cell that expresses little or no B7-H6. For example, where a normal (healthy) cell does not express detectable levels of B7-H6 and a diseased cell does express detectable levels of B7-H6, expression of B7-H6 by the diseased cell is characterized as "increased." Generally, a method of treatment includes administering a therapeutically effective amount of an antibody, antibody fragment or fusion protein to a subject. A therapeutically effective amount can be determined by a medical professional by known methods. For example, an antibody may be delivered to a subject at a dosage of 10 µg/kg to 1 mg/kg. Bispecific molecules may be delivered to a subject at a dosage of, for example, 100 ng/kg to 100 mg/kg. Cell comprising antibodies or antibody fragments may be delivered to subject at in an amount of, for example, $5 \times 10^7$-$5 \times 10^9$ (e.g., $5 \times 10^8$) cells. In some embodiments, an effective amount is an amount effective to reduce the growth of B7-H6-expressing (e.g., cancerous) cells by at least 20% relative to untreated control cells. For example, an effective amount may be an amount effective to reduce the growth of B7-H6-expressing cells by at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99% or 100%. In some embodiments, an effective amount is an amount effective to reduce the growth of B7-H6-expressing cells by 10-100%, 20-100%, 30-100%, 40-100%, 50-100%, 60-100%, 70-1005, 80-100% or 90-100%.

In some embodiments, the contacted B7-H6 cells can be in, for example, a cell culture or animal model of a disorder associated with aberrant expression or amounts of B7-H6. These methods are useful, for example, for measuring and/or ranking (relative to another antibody) the antibody's inhibitory activity for a specific B7-H6 cell type. Cytotoxicity of an antibody, antibody fragment or fusion protein (e.g., BiTE) can be assessed using any conventional assay including, e.g., a lactate dehydrogenase cytotoxicity assay such as the CYTOTOX 96® non-radioactive cytotoxicity assay commercially available from PROMEGA®.

An antibody, or antigen-binding antibody fragment, used as provided herein can be any anti-B7-H6 antibody, or antigen-binding antibody fragment, of the present disclosure. Thus, the antibody can be chimeric, humanized, synthetic, F(ab)₂, Fv, scFv, F(ab')₂, F(ab), VL, VII, dsFv, Fv, or (scFv)₂, for example. In some embodiments, the methods include administering an IgG, an scFv, a dsFv, a F(ab')₂, a diabody, a bivalent antibody, a CAR, a BiTE or a DART that targets cells expressing B7-H6.

In some embodiments, a subject who is administered an anti-B7-H6 antibody, or antigen-binding antibody fragment, is a subject having a cancer, an autoimmune disorder or an immunodeficiency disorder (e.g., Sjogren's syndrome, see, e.g., Rusakiewicz et al. *Science Translational Medicine*, 5(195): 195, 2013). For example, as subject may have lymphoma (e.g., T-cell lymphoma or B-cell lymphoma), leukemia (e.g., myeloid leukemia, acute nonlymphocytic leukemia. T-cell acute lymphoblastic leukemia), melanoma or sarcoma (e.g., gastric sarcoma). In some embodiments, a subject who is administered an anti-B7-H6 antibody, or antigen-binding antibody fragment, is a subject having myeloid leukemia, acute nonlymphocytic leukemia, acute lymphoblastic leukemia, B-cell lymphoma, breast cancer, cervical cancer, clear cell renal cell carcinoma, dermatofibrosarcoma protuberans, gastric sarcoma, gastrointestinal stromal tumor, glioblastoma, leiomyosarcoma, invasive ductal breast carcinoma, malignant fibrous histiocytoma, melanoma, ovarian serous surface papillary carcinoma, pancreatic cancer, prostate cancer, T-cell acute lymphoblastic leukemia or T-cell lymphoma.

In some embodiments, a subject is administered an engineered (e.g., recombinant) immune cell (e.g., T cell) that expresses an antibody or antigen-binding antibody fragment that binds specifically to B7-H6 (e.g., adoptive transfer). In some embodiments, the immune cell (e.g., T cell) comprises a CAR or BiTE that selectively binds B7-H6 (e.g., an epitope of B7-H6 bound by an scFV of FIG. 2 or Table 2). Recombinant technology, for example, can be used to introduce CAR-encoding or BiTE-encoding genetic material into any suitable immune cell (e.g., T cell such as an effector memory T-cell from the subject). In some embodiments, a CAR is expressed on a T cell using methods that utilize viral delivery, transposons, plasmids and/or mRNA. These and other methods of expression are known in the art and are not intended to be limiting. If we need more detail in particular, it can be done too. T-cells carrying the genetic material can be expanded (e.g., in the presence of cytokines). The recombinant T-cells may be transferred, typically by infusion, to a subject. The transferred T cells can then mount an immune response against B7-H6-expressing cells in the subject. The adoptive transfer method can be used, for example, to treat subjects that have or are suspected of having a cancer, an autoimmune disorder or an immunodeficiency disorder as provided herein.

In some embodiments, methods further include co-administering a second therapeutic agent for a disorder associated with elevated B7-H6. For example, methods may further include co-administering a cytotoxic, cytostatic, or anti-angiogenic agent suitable for treating a cancer. If the cancer is a B-cell lymphoma, the method can further include, for example, co-administration of rituximab, alemtuzumab or a CHOP (cyclophosphamide, hydroxydaunorubicin, oncovin and prednisone (or prednisolone) chemotherapeutic regimen.

For use in treatment, the present disclosure also provides compositions (e.g., pharmaceutical compositions) comprising an antibody or antigen-binding antibody fragment that binds specifically to B7-H6 (e.g., an scFv of FIG. 2 or Table 2). Compositions can be prepared from any of the antibodies described herein. An example of a pharmaceutical composition includes an anti-B7-h6 scFv fused to anti-CD3e scFv via a flexible linker (a BiTE). Yet example of a pharmaceutical composition includes anti-B7-H6 scFv fused to the hinge, transmembrane and intracellular domains of CD28 and the intracellular domain of CD3zeta (a CAR).

In some embodiments, a composition (e.g., a pharmaceutical composition) includes a carrier for the antibody, such as a pharmaceutically acceptable carrier. A pharmaceutically acceptable carrier can be any suitable pharmaceutically acceptable carrier. The term "pharmaceutically acceptable carrier," refers to one or more compatible solid or liquid fillers, diluents, other excipients, or encapsulating substances, which are suitable for administration into a human or veterinary subject (e.g., a physiologically acceptable carrier or a pharmacologically acceptable carrier). The term "carrier" denotes an organic or inorganic ingredient, natural or synthetic, with which the active ingredient is combined to facilitate the application. The pharmaceutically acceptable carrier can be co-mingled with one or more of the active components, e.g., a hybrid molecule, and with each other, when more than one pharmaceutically acceptable carrier is present in the composition in a manner so as not to substantially impair the desired pharmaceutical efficacy. "Pharmaceutically acceptable" materials typically are capable of administration to a patient without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

A pharmaceutical composition can contain, in some embodiments, suitable buffering agents, including, for example, acetic acid in a salt, citric acid in a salt, boric acid in a salt, and phosphoric acid in a salt. Pharmaceutical compositions also may contain suitable preservatives, such as benzalkonium chloride, chlorobutanol, parabens, thimerosal, or a combination thereof.

A pharmaceutical composition can be presented in unit dosage form and can be prepared by any suitable method, many of which are well-known. Such methods include the step of bringing an anti-B7-H6 antibody into association with a carrier that constitutes one or more accessory ingredients. In general, a composition is prepared by bringing the active agent into association with a liquid carrier, a finely divided solid carrier, or both, and then, if necessary, shaping the composition.

A composition suitable for parenteral administration includes, for example, a sterile aqueous preparation of the composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent. Among the acceptable vehicles and solvents that can be employed are water, Ringer's solution, and isotonic sodium chloride solution. In some embodiments, an anti-B7-H6 antibody composition is formulated and pre-packaged for subcutaneous injection in the form of a pen (e.g., single-use pen) or syringe (e.g., single-use syringe). Other forms of preparation and delivery systems are encompassed by the present disclosure.

A "subject" may be an animal subject, such as a human subject. Animal subjects include, but are not limited to, animal models, such as, mammalian models of conditions or disorders associated with elevated B7-H6 expression such as those described above.

Also provided herein are uses of anti-B7-H6 antibodies to detect in a test sample an altered amount of B7-H6 (e.g., cell surface B7-H6), for example, relative to a control. A test sample can be from a cell culture or from a test subject, e.g., a plasma or a tissue sample from a subject that has, is suspected to have, or is at risk for a disease or condition characterized by aberrant expression of B7-H6 in a subject. A control amount may correspond to the B7-H6 amount detected using the same antibody in a corresponding sample(s) from one or more control cultures or subjects. Methods of using anti-B7-H6 antibodies to determine B7-H6 amounts can include any immunoassay such as immuno-(western) blot, enzyme-linked immunosorbent assay (ELISA), and flow cytometry, e.g., fluorescence-activated cell sorting (FACS) analysis.

Additionally, B7-H6 detection can be used to monitor the progress of a disorder associated with B7-H6 expression. Amounts of B7-H6 that are significantly elevated or decreased relative to control indicate that the subject's disorder is deteriorating or improving, respectively.

The foregoing screens can be used to identify the presence or to monitor the progress of disorders, including those described above.

The invention also provides kits suitable for carrying out the methods of the invention. Typically, a kit includes two or more components required for performing a therapeutic or detection method of the invention. Kit components include, but are not limited to, one or more antibody of the invention, appropriate reagents, and/or equipment.

Also provided herein are kits that can include an anti-B7-H6 antibody and an immunoassay buffer suitable for detecting B7-H6 (e.g., by ELISA or FACS). The kit may also at least one microliter plate, standard, assay diluent, wash buffer, adhesive plate cover, and/or instructions for carrying out a method using the kit. The kit can include an antibody bound to a substrate (e.g., a multi-well plate or a chip), which is suitably packaged and useful for detecting B7-H6. In some embodiments, a kit includes an anti-B7-H6 antibody that is conjugated to a label, such as, a fluorescent label, a biologically active enzyme label, a luminescent label, or a chromophore label. A kit can further include reagents for visualizing the conjugated antibody, e.g., a substrate for the enzyme. In some embodiments, a kit includes an anti-B7-H6 antibody that is conjugated to a contrast agent and, optionally, one or more reagents or pieces of equipment useful for imaging the antibody in a subject. Generally the antibody of the invention in a kit is suitably packaged, e.g., in a vial, pouch, ampoule, and/or any container appropriate for a therapeutic or detection method. Kit components can be provided as concentrates (including lyophilized compositions), which may be further diluted prior to use or they can be provided at the concentration of use. When an anti-B7-H6 antibody is for use in vivo, single dosages may be provided in sterilized containers having the desired amount and concentration of agents.

Embodiments of the present disclosure are described in more detail by the following non-limiting examples.

EXAMPLES

Example 1: Human scFvs Targeting Tumor Antigen B7H6

Fully human scFvs against tumor antigen B7H6 were produced from a nonimmune library of $10^9$ human antibody scFv fragments cloned and expressed on the surface of yeast. Magnetic bead and single-cell sorting methods with positive selections for binding to B7H6-Ig, a fusion protein containing the extracellular portion of B7H6 and the Fc portion of a Mouse IgG2a, and negative selections for binding to a polyclonal mixture of Normal Mouse IgG were used. One round of random mutagenesis to isolate the clones described below was also performed.

Figure 1:
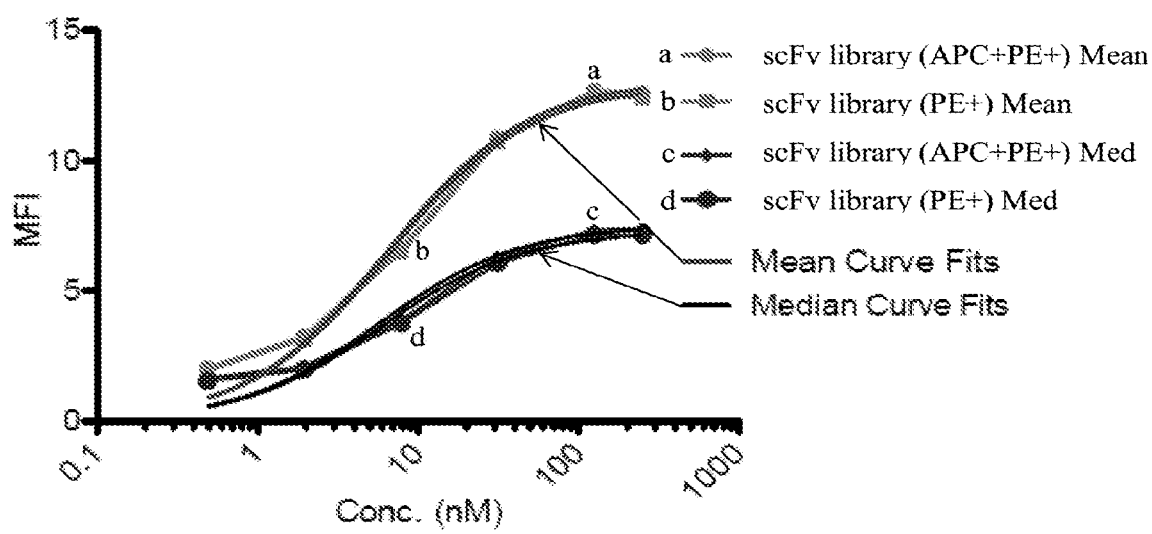
FIG. 1 is a graph showing that binding of yeast-displayed scFvs to soluble B7H6-1 g antigen demonstrates a bulk library KD in the nanomolar range. Fluorophores APC and PE reflect expression tag and antigen-binding signal, respectively. Plots are shown for library populations gated for antigen binding (PE+) and for both expression and antigen binding (APC+PE+). No significant difference was observed for the double positive vs. single positive gates.

The scFvs, denoted generation 2.5 (Lib g2.5), showed 10-50 nM affinity as demonstrated in FIG. 1. From this generation, four distinct scFvs (sequence alignment shown in FIG. 2 and full sequences listed in Table 2) belonging to the same clonal family, defined as scFV's sharing IgH VS (specifically IgHV1 & IgHJ3/4) and IgL VJ (IgLV2 & IGLJ7/3) usage with identical CDR3 lengths, were affinity matured/regressed to generate a panel of fully human B7H6-targeting scFvs with a range of affinities for Chimeric-Antigen-Receptor (CAR)-T Cell testing. Table 1 demonstrates the number of amino acid differences between isolated scFvs, which range from 1-4 residue differences. Additionally, these scFvs recognized an epitope distinct from mouse antibody TZ47, as demonstrated by competitive binding assays shown in FIG. 4.

TABLE 1

Protein Sequence Distance Matrix: number of amino acid differences between each pair of variant.

|        | g2.5-9 | g2.5-6 | g2.5-3 | g2.5-2 |
|--------|--------|--------|--------|--------|
| g2.5-9 | —      | 3      | 1      | 3      |
| g2.5-6 | 3      | —      | 2      | 4      |
| g2.5-3 | 1      | 2      | —      | 2      |
| g2.5-1 | 3      | 4      | 2      | —      |

Experimental Validation of scFvs as Soluble scFv-Fc Proteins.

Isolated scFvs were grafted onto VRC01 IgG1 antibody heavy chain constant regions (CH1-CH3) to obtain soluble scFv-Fc for testing. One representative clone, g2.5-11 (equivalent to Fg2.5-3 at the amino acid level), was expressed recombinantly in Human Embryonic Kidney (HEK) cells for soluble secretion. Purified scFv-Fc proteins were then screened for binding to both B7H6-expressing cell lines and soluble B7H6 antigen.

Production/Purification of Fv-Fc.

The representative g2.5-11 scFv-Fc was expressed recombinantly and purified. Briefly, HEK-293F cells at a density of $10^6$ cells/mL were transfected with pCMVR-g2.5-11-Fe plasmids at a concentration of 1.0 mg/L and cultured for 5 days before Protein A purification of cell culture supernatants. Cultures were centrifuged at 3,000×g for 15 minutes and supernatants were passed over 1.0 mL Protein A resin columns. Columns were then washed with 10 mL phosphate-buffered saline (PBS) before elution with 100 mM glycine, pH 3. Eluants were then buffer-exchanged back into PBS using Amicon-30K ultracentrifugation tubes.

g2.5-11 scFv-Fc Binds B7H6-Expressing Cell Line RMA-B7H6 with KD~30 nM Affinity and does not Bind Negative Control RMA Cell Line.

Figure 3B:
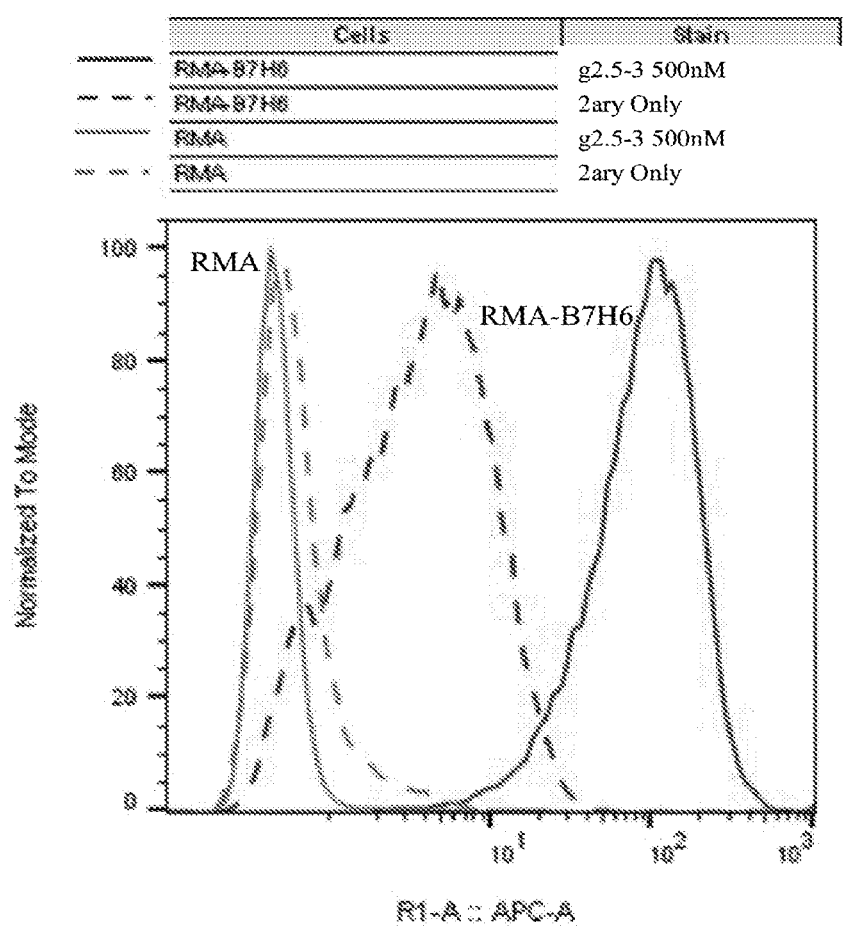
FIG. 3B shows raw flow cytometry data for the titration curves presented in FIG. 3, demonstrating specificity for RMA-B7H6 over RMA at a single concentration (500 nM).

A Miltenyi Biotech MACSQuant® Flow Cytometer was used for cell-binding assays. To obtain an experimental $K_D$, 2.5E5 RMA-B7H6 (B7H6-expressing) or RMA (negative control) cells/well were washed 3 times with PBS+0.1% BSA(PBS-F) before pre-incubation with 0-500 nM g2.5-11. Cells were then washed 3 times with PBS-F before secondary detection reagents were added. After a final wash with PBS-F, cells were resuspended in 200 mL PBS-Elwell before reading on a Miltenyi MACSQuant® flow cytometer. Results, shown in FIGS. 3A and 3B, demonstrated binding to RMA-B7H6 cells with KD ~20 nM and negligible binding to RMA cells.

g2.5-11 scFv-Fc Binds an Epitope on B7H6 that is Distinct from Murine Antibody TZ47.

Figure 4B:
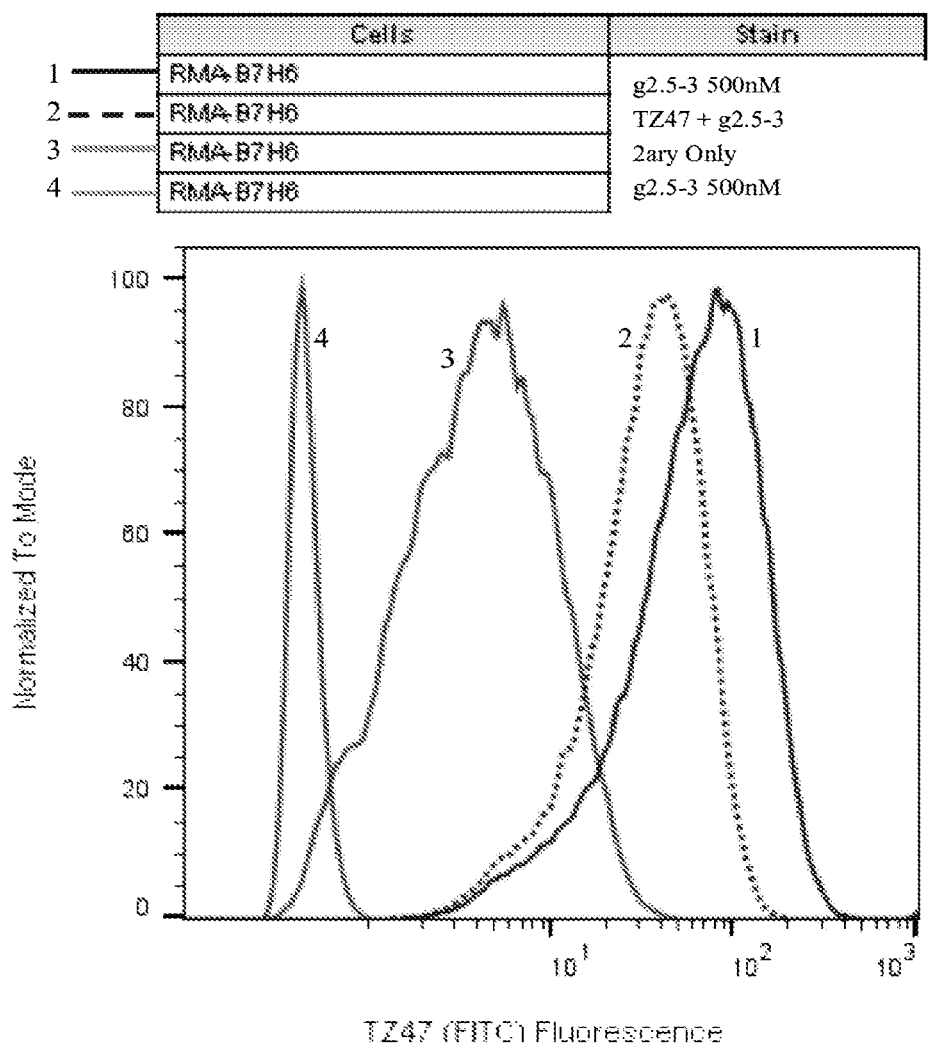

For the competition assay, 2.5E5 RMA-B7H6 cells/well were washed 3× with PBS+0.1% BSA (PBS-F) before incubation with 500 nM of either g2.5-11 scFv-Fc, murine TZ47, or both for 1 hour. Cells were then washed 3 times with PBS-F before secondary detection reagents were added to measure the gain or loss of signal for g2.5-11 scFv-Fc (APC), and the competing murine TZ47 (FITC). After a final wash with PBS-F, cells were resuspended in 200 mL PBS-F/well before reading on a Miltenyi MACSQuant® flow cytometer. FIGS. 4A and 4B demonstrate that binding of each scFv-Fc/anti body was not significantly affected by the addition of the other.

g2.5-11 scFv-Fc Binds Soluble B7H61 g Antigen.

Figure 5:
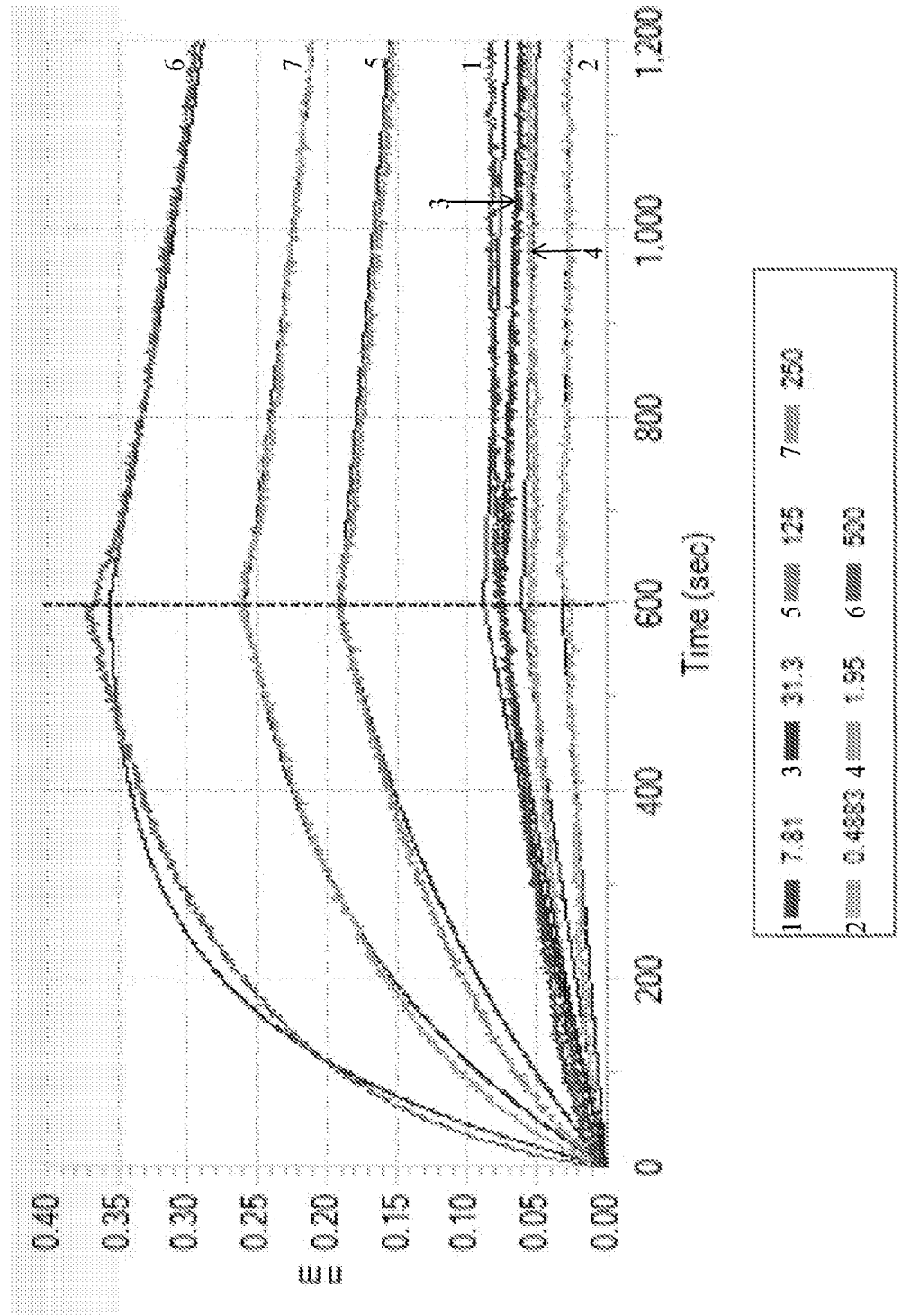
FIG. 5 shows by Octet BioLayer Interferometry (BLI) measurement of the binding of g2.5-11 scFV-Fc to soluble antigen B7H61 g. Global fits kinetic constants are as follows: $K_D$=2.57E-08M (25.7 nM), $R^2$=0.996178, $K_{on}$=1.37E+4/Ms, and $K_{dis}$=3.50E-04.

Anti-Human CH1 tips were activated with 0.05 mg/mL g2.5-11 scFv-Fc protein for 600 seconds to ensure saturation of tips with antigen. Tips were then transferred to PBS+0.1% Tween (PBS-T)-containing wells for baseline measurements of scFv-Fc-loaded tips before transferring to antigen-containing wells ranging from 0-500 nM B7H6-Ig. Samples were double-referenced using non-activated tips and PBS-T only containing wells. The Octet Analysis software was used for global kinetic fits which determine a single KD measurement for each antigen using association and dissociation curves for all concentrations tested. The quality of fits were determined by $R^2$ correlation coefficients and are reported in FIG. 5.

Testing of g2.5-6 as a Fv Binding Region for a Chimeric Antigen Receptor (CAR).

Figure 6:
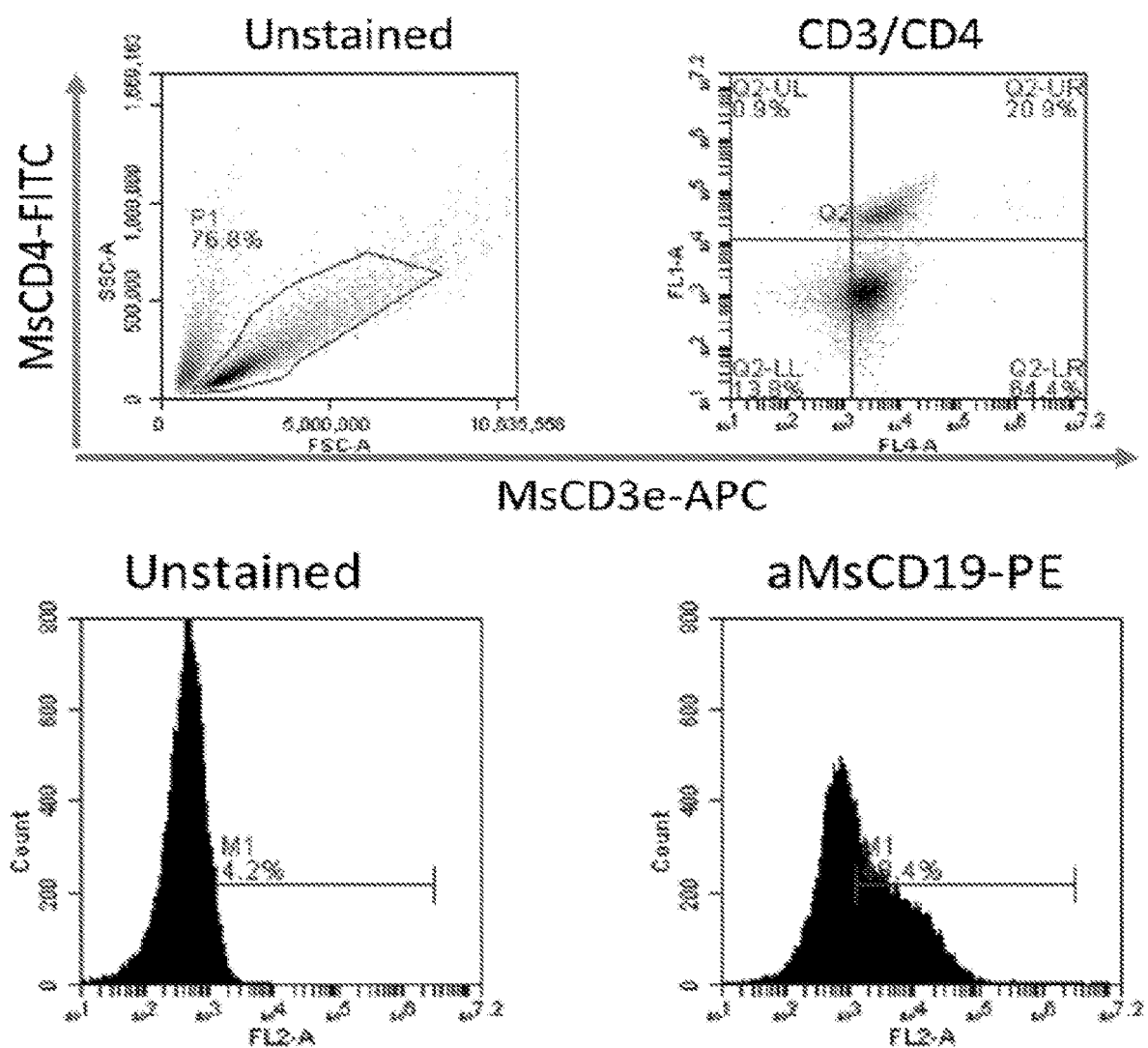
FIG. 6 shows expression of CD4 and CD3 on transduced murine T cells analyzed on day 8 following transduction and selection. CD19 expression on the T cells is indicative of viral transduction.
Figure 7:
FIG. 7 shows the amount of IFN-gamma in the cell-free media as determined by ELISA. T cells were co-cultured with media, RMA or RMA-B7H6 tumor cells overnight. A B7H6-specific CAR was used as a positive control on T cells (pos ctrl CAR), and g2.5-6 CD28-3z CAR was tested.

The Fv region from clone g2.5-6 was cloned into a CAR backbone containing the hinge, transmembrane and cytoplasmic region from human CD28 connected to the cytoplasmic region of CD3z. This new CAR contains the binding of g2.5-6 for B7H6, a costimulation signal from CD28 and a primary signal for T cells via CD3zeta. This CAR was expressed in T cells using a retroviral vector that also contains a truncated mouse CD19 gene for cell tracking. As shown in FIG. 6, the g2.5-6-based CAR vector is expressed in murine T cells after transduction (see CD19 expression). These g2.5-6 CAR T cells were co-cultured with RMA or RMA-B7H6 tumor cells or media for 24 hours and the amount of IFN-gamma produced was determined by ELISA. Only when B7H6 was expressed on the tumor cell was IFN-gamma produced (FIG. 7). As a positive control, another CAR was used that also recognizes B7H6.

Specific Lysis of B7H6+ Tumor Cells by Fg2.5 CAR T Cells.

Specific Lysis of B7H6+ Tumor Cells by Fg2.5 CAR T Cells.

Figure 8A:
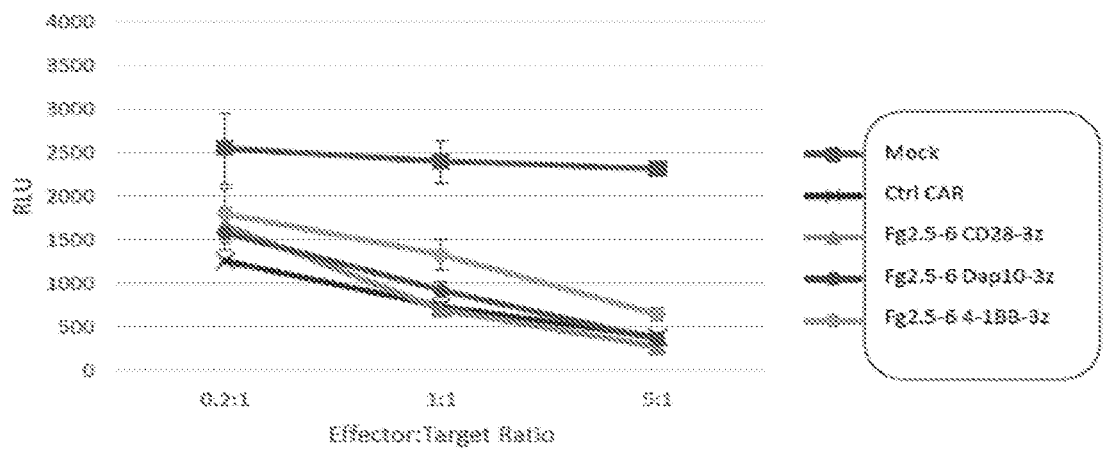
FIGS. 8A and 8B shows that g2.5-6 CAR T cells having a CD3zeta cytoplasmic domain and a CD28 costimulatory domain, a Dap10 costimulatory domain, or a 4-1BB costimulatory domain exhibit anti-tumor lytic activity in the presence of RMA B7H6 tumor cells (FIG. 8A) but not in the presence of RMA cells (FIG. 8B).
Figure 8B:
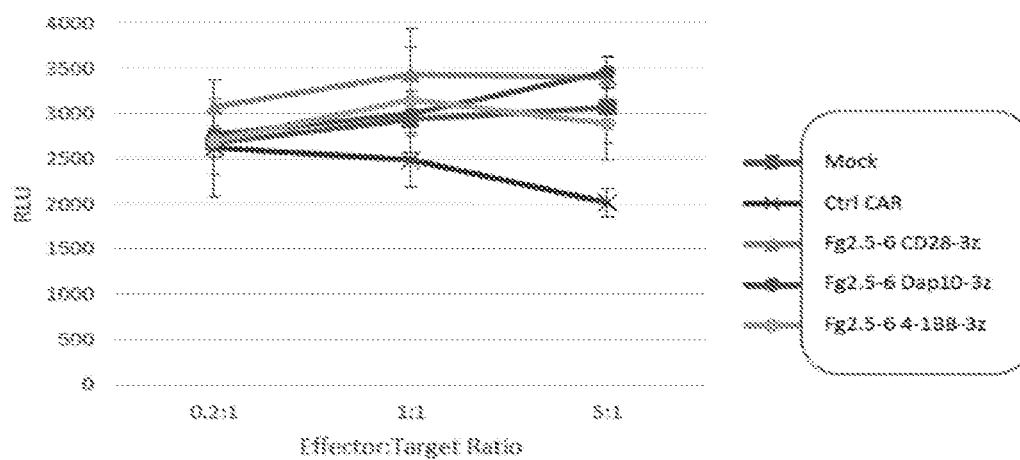

Effector T cells were cultured with RMA (FIG. 8A) or RMA-B7H6 (FIG. 8B) tumor cells for 24 hours. T cells expressed B7H6-specific CARs with different costimulatory domains (CD28, Dap10, or 4-1BB) and the CD3zeta cytoplasmic domain. The tumor cells expressed luciferase. The decrease in light signal (RLU) is an indication of less tumor survival (tumor cell lysis). The B7H6-specific CAR T cells were able to kill the B7H6⁺ tumor cells but not the B7H6-negative tumor cells. The control CAR (Ctrl CAR) is a human B7H6-specific CAR (based on the Fv from the TZ47 murine antibody) that recognizes a different epitope on B7H6. Mock T cells are activated T cells that do not express a CAR. These data show that the B7H6-specific CAR T cells exhibit anti-tumor lytic activity.

TABLE 2

Antibody scFv Amino Acid Sequences

| Name | Sequence | SEQ ID NO: |
|---|---|---|
| g2.5-9 (G4S)3 Linker in bold | QVQLVQSGAEVKKPGASVKISCKASGYTLGTYTLHWMRQAPG QRIEWMGWINPGNGYTKYSQRLQGRVTINRDTSATTTYMELSS LRSEDTAVYFCATDRAPVRRAFDIWGQGTMVTVSSGILGSGG GGSGGGGSGGGGSQSVLTQPASVSGSPGQSVTISCTGTSSDIGS YKFVSWYQHHPGKAPKLMIYDVTQRPSGVPYRFSGSKSGNTAS LTISGLQAEDEADYYCCSYAGDYTYALFGGGTQLTVLS | 1 |
| g2.5-9 Heavy Chain | QVQLVQSGAEVKKPGASVKISCKASGYTLGTYTLHWMRQAPG QRIEWMGWINPGNGYTKYSQRLQGRVTINRDTSATTTYMELSS LRSEDTAVYFCATDRAPVRRAFDIWGQGTMVTVSS | 2 |
| g2.5-9 Light Chain | QSVLTQPASVSGSPGQSVTISCTGTSSDIGSYKFVSWYQHHPGK APKLMIYDVTQRPSGVPYRFSGSKSGNTASLTISGLQAEDEADY YCCSYAGDYTYALFGGGTQLTVLS | 3 |
| g2.5-9 CDR-H1 | GYTLGTYT | 4 |
| g2.5-9 CDR-H2 | INPGNGYT | 5 |
| g2.5-9 CDR-H3 | ATDRA | 6 |
| g2.5-9 CDR-L1 | SSDIGSYKF | 7 |
| g2.5-9 CDR-L2 | DVT | 8 |
| g2.5-9 CDR-L3 | CSYAGDYTYAL | 9 |
| g2.5-6 | QVQLVQSGAEVKKPGASVKIPCKASGYTLGTYTLHWMRQAPG QRIEWMGWINPGNGYTKYSQRFQGRVTINRDTSATTTYMELSS LRSEDTAVYFCATDRAPVRRAFDIWGQGTMVTVSSGILGSGG GGSGGGGSGGGGSQSVLTQPASVSGSPGQSVTISCTGTSSDIGS YKFVSWYQHHPGKAPKLMIYDVTQRPSGVPYRFSGSKSGNTAS LTISGLQAEDEADYYCCLYAGDYTYALFGGGTQLTVLS | 10 |
| g2.5-6 Heavy Chain | QVQLVQSGAEVKKPGASVKIPCKASGYTLGTYTLHWMRQAPG QRIEWMGWINPGNGYTKYSQRFQGRVTINRDTSATTTYMELSS LRSEDTAVYFCATDRAVRRAFDIWGQGTMVTVSS | 11 |
| g2.5-6 Light Chain | QSVLTQPASVSGSPGQSVTISCTGTSSDIGSYKFVSWYQHHPGK APKLMIYDVTQRPSGVPYRFSGSKSGNTASLTISGLQAEDEADY YCCLYAGDYTYALFGGGTQLTVLS | 12 |
| g2.5-6 CDR-H1 | GYTLGTYT | 13 |
| g2.5-6 CDR-H2 | INPGNGYT | 14 |
| g2.5-6 CDR-H3 | ATDRA | 15 |
| g2.5-6 CDR-L1 | SSDIGSYKF | 16 |
| g2.5-6 CDR-L2 | DVT | 17 |
| g2.5-6 CDR-L3 | CLYAGDYTYAL | 18 |

TABLE 2-continued

Antibody scFv Amino Acid Sequences

| Name | Sequence | SEQ ID NO: |
|---|---|---|
| g2.5-3* | QVQLVQSGAEVKKPGASVKISCKASGYTLGTYTLHWMRQAPG QRIEWMGWINPGNGYTKYSQRFQGRVTINRDTSATTTYMELSS LRSEDTAVYFCATDRAPVRRAFDIWGQGTMVTVSSGILGSGG GGSGGGGSGGGGSQSVLTQPASVSGSPGQSVTISCTGTSSDIGS YKFVSWYQHHPGKAPKLMIYDVTQRPSGVPYRFSGSKSGNTAS LTISGLQAEDEADYYCCSYAGDYTYALFGGGTQLTVLS *the amino acid sequence for g2.5-3 and g2.5-11 are identical | 19 |
| g2.5-3 Heavy Chain | QVQLVQSGAEVKKPGASVKISCKASGYTLGTYTLHWMRQAPG QRIEWMGWINPGNGYTKYSQRFQGRVTINRDTSATTTYMELSS LRSEDTAVYFCATDRAPVRRAFDIWGQGTMVTVSS | 20 |
| g2.5-3 Light Chain | QSVLTQPASVSGSPGQSVTISCTGTSSDIGSYKFVSWYQHHPGK APKLMIYDVTQRPSGVPYRFSGSKSGNTASLTISGLQAEDEADY YCCSYAGDYTYALFGGGTQLTVLS | 21 |
| g2.5-3 CDR-H1 | GYTLGTYT | 22 |
| g2.5-3 CDR-H2 | INPGNGYT | 23 |
| g2.5-3 CDR-H3 | ATDRA | 24 |
| g2.5-3 CDR-L1 | SSDIGSYKF | 25 |
| g2.5-3 CDR-L2 | DVT | 26 |
| g2.5-3 CDR-L3 | CSYAGDYTYAL | 27 |
| g2.5-1 | QVQLVQSGAEVKKPGASVKISCKASGYTPGTYTLHWMRQAPG QRIEWMGWINPGNGYTKYSQRFQARVTINRDTSATTTYMELSS LRSEDTAVYFCATDRAPVRRAFDIWGQGTMVTVSSGILGSGG GGSGGGGSGGGGSQSVLTQPASVSGSPGQSVTISCTGTSSDIGS YKFVSWYQHHPGKAPKLMIYDVTQRPSGVPYRFSGSKSGNTAS LTISGLQAEDEADYYCCSYAGDYTYALFGGGTQLTVLS | 28 |
| g2.5-1 Heavy Chain | VQLVQSGAEVKKPGASVKISCKASGYTPGTYTLHWMRQAPGQ RIEWMGWINPGNGYTKYSQRFQARVTINRDTSATTTYMELSSL RSEDTAVYFCATDRAPVRRAFDIWGQGTMVTVSS | 29 |
| g2.5-1 Light Chain | QSVLTQPASVSGSPGQSVTISCTGTSSDIGSYKFVSWYQHHPGK APKLMIYDVTQRPSGVPYRFSGSKSGNTASLTISGLQAEDEADY YCCSYAGDYTYALFGGGTQLTVLS | 30 |
| g2.5-1 CDR-H1 | GYTLGTYT | 31 |
| g2.5-1 CDR-H2 | INPGNGYT | 32 |
| g2.5-1 CDR-H3 | ATDRA | 33 |
| g2.5-1 CDR-L1 | SSDIGSYKF | 34 |
| g2.5-1 CDR-L2 | DVT | 35 |
| g2.5-1 CDR-L3 | CSYAGDYTYAL | 36 |
| Consensus Sequence | QVQLVQSGAEVKKPGASVKISCKASGYTLGTYTLHWMRQAPG QRIEWMGWINPGNGYTKYSQRFQGRVTINRDTSATTTYMELSS LRSEDTAVYFCATDRAPVRRAFDIWGQGTMVTVSSGILGSGG GGSGGGGSGGGGSQSVLTQPASVSGSPGQSVTISCTGTSSDIGS YKFVSWYQHHPGKAPKLMIYDVTQRPSGVPYRFSGSKSGNTAS LTISGLQAEDEADYYCCSYAGDYTYALFGGGTQLTVLS | 37 |

TABLE 3

Antibody scFv Nucleic Acid Sequences

| Name | Sequence | SEQ ID NO: |
|---|---|---|
| g2.5-9 (G4S)3 Linker in bold | CAGGTCCAGCTTGTACAGTCTGGGGCTGAGGTGAAGAAGCC TGGGGCCTCAGTGAAGATTTCCTGCAAGGCTTCTGGATACAC CCTCGGTACCTACACTCTGCACTGGATGCGCCAGGCCCCCGG ACAAAGGATTGAGTGGATGGGATGGATCAACCCTGGCAATG GTTACACAAAATATTCACAGAGGCTCCAGGGCAGAGTCACC ATTAATAGGGACACATCCGCGACCACAACGTACATGGAGCT GAGCAGCCTGAGATCTGAAGACACGGCTGTATATTTCTGTGC GACAGATAGGGCTCCAGTTCGTCGTGCTTTTGATATCTGGGG CCAAGGGACAATGGTCACCGTCTCTTCAGGAATTCTAGGAT CCGGTGGCGGTGGCAGCGGCGGTGGTGGTTCCGGAGGC GGCGGTTCTCAGTCTGTTCTGACTCAGCCTGCCTCCGTGTCT GGGTCTCCTGGACAGTCGGTCACCATCTCCTGCACTGGCACC AGCAGTGACATTGGTTCTTATAAATTTGTCTCCTGGTACCAA CATCACCCCGGCAAAGCCCCCAAACTCATGATTTATGACGTC ACTCAGCGGCCCTCAGGGGTCCCTTATCGCTTCTCTGGCTCC AAGTCTGGCAACACGGCCTCCCTGACCATCTCTGGGCTCCAG GCTGAAGATGAGGCTGATTATTACTGCTGCTCATATGCAGGC GACTACACTTATGCTCTATTCGGAGGAGGCACCCAGCTGACC GTCCTCTCC | 38 |
| g2.5-6 | CAGGTCCAGCTTGTACAGTCTGGGGCTGAGGTGAAGAAGCC TGGGGCCTCAGTGAAGATTCCCTGCAAGGCTTCTGGATACAC CCTCGGTACCTACACTCTGCACTGGATGCGCCAGGCCCCCGG ACAAAGGATTGAGTGGATGGGATGGATCAACCCTGGCAATG GTTACACAAAATATTCACAGAGGTTCCAGGGCAGAGTCACC ATTAATAGGGACACATCCGCGACCACAACGTACATGGAGCT GAGCAGCCTGAGATCTGAAGACACGGCTGTATATTTCTGTGC GACAGATAGGGCTCCAGTTCGTCGTGCTTTTGATATCTGGGG CCAAGGGACAATGGTCACCGTCTCTTCAGGAATTCTAGGAT CCGGTGGCGGTGGCAGCGGCGGTGGTGGTTCCGGAGGC GGCGGTTCTCAGTCTGTTCTGACTCAGCCTGCCTCCGTGTCT GGGTCTCCTGGACAGTCGGTCACCATCTCCTGCACTGGCACC AGCAGTGACATTGGTTCTTATAAATTTGTCTCCTGGTACCAA CATCACCCCGGCAAAGCCCCCAAACTCATGATTTATGATGTC ACTCAGCGGCCCTCAGGGGTCCCTTATCGCTTCTCTGGCTCC AAGTCTGGCAACACGGCCTCCCTGACCATCTCTGGGCTCCAG GCTGAAGATGAGGCTGATTATTACTGCTGCTTATATGCAGGC GACTACACTTATGCTCTATTCGGAGGAGGCACCCAGCTGACC GTCCTCTCC | 39 |
| g2.5-3 | CAGGTCCAGCTTGTACAGTCTGGGGCTGAGGTGAAGAAGCC TGGGGCCTCAGTGAAGATTTCCTGCAAGGCTTCTGGATACAC CCTCGGTACCTACACTCTGCACTGGATGCGCCAGGCCCCCGG ACAAAGGATTGAGTGGATGGGATGGATCAACCCTGGCAATG GTTACACAAAATATTCACAGAGGTTCCAGGGCAGAGTCACC ATTAATAGGGACACATCCGCGACCACAACGTACATGGAGCT GAGCAGCCTGAGATCTGAAGACACGGCTGTATATTTCTGTGC GACAGATAGGGCTCCAGTTCGTCGTGCTTTTGATATCTGGGG CCAAGGGACAATGGTCACCGTCTCTTCAGGAATTCTAGGAT CCGGTGGCGGTGGCAGCGGCGGTGGTGGTTCCGGAGGC GGCGGTTCCCAGTCTGTTCTGACTCAGCCTGCCTCCGTGTCT GGGTCTCCTGGGCAGTCGGTCACCATCTCCTGCACTGGCACC AGCAGTGACATTGGTTCTTATAAATTTGTCTCCTGGTACCAA CATCACCCCGGCAAAGCCCCCAAACTCATGATTTATGATGTC ACTCAGCGGCCCTCAGGGGTCCCTTATCGCTTCTCTGGCTCC AAGTCTGGCAACACGGCTTCCCTGACCATCTCTGGGCTCCAG GCTGAAGATGAGGCTGATTATTACTGCTGCTCATATGCAGGC GACTACACTTATGCTCTATTCGGAGGAGGCACCCAGCTGACC GTCCTCTCC | 40 |
| g2.5-1 | AGGTCCAGCTTGTACAGTCTGGGGCTGAGGTGAAGAAGCCT GGGGCCTCAGTGAAGATTTCCTGCAAGGCTTCTGGATACACC CCCGGTACCTACACTCTGCACTGGATGCGCCAGGCCCCCGGA CAAAGGATTGAGTGGATGGGATGGATCAACCCTGGCAATGG TTACACAAAATATTCACAGAGGTTCCAGGCCAGAGTCACCAT TAATAGGGACACATCCGCGACCACAACGTACATGGAGCTGA GCAGCCTGAGATCTGAAGACACGGCTGTATATTTCTGTGCGA CAGATAGGGCTCCAGTTCGTCGTGCTTTTGATATCTGGGGCC AAGGGACAATGGTCACCGTCTCTTCAGGAATTCTACGATCC GGTGGCGGTGGCAGCGGCGGTGGTGGTTCCGGAGGCGG CGGTTCTCAGTCTGTTCTGACTCAGCCTGCCTCCGTGTCTGG GTCTCCTGGACAGTCGGTCACCATCTCCTGCACTGGCACCAG CAGTGACATTGGTTCTTATAAATTTGTCTCCTGGTACCAACA TCACCCCGGCAAAGCCCCCAAACTCATGATTTATGATGTCAC TCAGCGGCCCTCAGGGGTCCCTTATCGCTTCTCTGGCTCCAA | 41 |

TABLE 3-continued

Antibody scFv Nucleic Acid Sequences

| Name | Sequence | SEQ ID NO: |
|---|---|---|
| | GTCTGGCAACACGGCCTCCCTGACCATCTCTGGGCTCCAGGC TGAAGATGAGGCTGATTATTATTGCTGCTCATATGCAGGCGA CTACACTTATGCTCTATTCGGAGGAGGCACCCAGCTGACCGT CCTCTCC | |
| g2.5-11 | CAGGTCCAGCTTGTACAGTCTGGGGCTGAGGTGAAGAAGCC TGGGGCCTCAGTGAAGATTTCCTGCAAGGCTTCTGGATACAC CCTCGGTACCTACACTCTGCACTGGATGCGCCAGGCCCCAG ACAAAGGATTGAGTGGATGGGATGGATCAACCCTGGCAATG GTTACACAAAATATTCACAGAGGTTCCAGGGCAGAGTCACC ATTAATAGGGACACATCCGCGACCACAACGTACATGGAGCT GAGCAGCCTGAGATCTGAAGACACGGCTGTATATTTCTGTGC GACAGATAGGGCTCCAGTTCGTCGTGCTTTTGATATCTGGGG CCAAGGGACAATGGTCACCGTCTCTTCAGGAATTCTAGGAT CCGGTGGCGGTGGCAGCGGCGGTGGTGGTTCCGGAGGC GGCGGTTCTCAGTCTGTTCTGACTCAGCCTGCCTCCGTGTCT GGGTCTCCTGGACAGTCGGTCACCATCTCCTGCACTGGCACC AGCAGTGACATTGGTTCTTATAAATTTGTCTCCTGGTACCAA CATCACCCCGGCAAAGCCCCCAAACTCATGATTTATGATGTC ACTCAGCGGCCCTCAGGGGTCCCTTATCGCTTCTCTGGCTCC AAGTCTGGCAACACGGCCTCCCTGACCATCTCTGGGCTCCAG GCTGAAGATGAGGCTGATTATTACTGCTGCTCATATGCAGGC GACTACACTTATGCTCTATTCGGAGGAGGCACCCAGCTGACC GTCCTCTCC | 42 |

What is claimed is:

1. An antibody or antigen-binding antibody fragment that binds specifically to B7 homolog 6 (B7-H6) which comprises either of the following: I. (a) a heavy chain variable region comprising, (i) a CDR1 of SEQ ID NO: 31, (ii) a CDR2 of SEQ ID NO: 32, and (iii) a CDR3 of SEQ ID NO: 33; and (b) a light chain variable region comprising, (i) a CDR1 of SEQ ID NO: 34, (ii) a CDR2 of SEQ ID NO: 35, and (iii) a CDR3 of SEQ ID NO: 36; or II. (a) a heavy chain variable region comprising, (i) a CDR1 of SEQ ID NO: 22, (ii) a CDR2 of SEQ ID NO: 23, and (iii) a CDR3 of SEQ ID NO: 24; and (b) a light chain variable region comprising, (i) a CDR1 of SEQ ID NO:
25, (ii) a CDR2 of SEQ ID NO: 26, and (iii) a CDR3 of SEQ ID NO: 27.

2. The antibody or antigen-binding antibody fragment of claim 1, wherein:
the antibody of (i) comprises a variable heavy chain having an amino acid sequence at least 90% identical to SEQ ID NO: 20 and a variable light chain having an amino acid sequence at least 90% identical to SEQ ID NO: 20; or the antibody of (ii) comprises a variable heavy chain having an amino acid sequence at least 90% identical to SEQ ID NO: 29 and a variable light chain having an amino acid sequence at least 90% identical to SEQ ID NO: 30.

3. The antibody, or antigen-binding antibody fragment, of claim 1, wherein the antibody is a full-length antibody or the antigen-binding fragment comprises a scFv fragment.

4. The antibody, or antigen-binding antibody fragment, of claim 1, wherein the antibody, or antigen-binding antibody fragment, is conjugated to a synthetic molecule.

5. The antibody, or antigen-binding antibody fragment, of claim 4, wherein the antibody, or antigen-binding antibody fragment, is a chimeric antigen receptor and the synthetic molecule comprises a transmembrane domain and an intracellular signaling domain.

6. The antibody, or antigen-binding antibody fragment, of claim 5, further comprising the intracellular domain of a costimulatory protein receptor.

7. The antibody, or antigen-binding antibody fragment of claim 4, wherein the antibody, or antigen-binding antibody fragment, is a bi-specific T-cell engager and the synthetic molecule comprises an antigen binding domain which binds to a T-cell antigen.

8. The antibody, or antigen-binding antibody fragment of claim 4, wherein the synthetic molecule is a label, a cytotoxic agent or a therapeutic radioisotope.

9. A nucleic acid encoding the antibody, or antigen-binding antibody fragment of claim 1 or a CAR or bi-specific T-cell engager comprising said antibody, or antigen-binding antibody fragment or a vector comprising said nucleic acid.

10. A recombinant cell comprising a CAR or bi-specific T-cell engager comprising an antibody, or antigen-binding antibody fragment according to claim 1.

11. A pharmaceutical composition or kit comprising the antibody, or antigen-binding antibody fragment of claim 1 and a pharmaceutically acceptable carrier.

12. A pharmaceutical composition or kit comprising the recombinant cell of claim 10 and a pharmaceutically acceptable carrier.

13. A chimeric antigen receptor comprising (a) an antigen-binding antibody fragment of claim 1, (b) a transmembrane domain, and (c) an intracellular signaling domain.

14. The chimeric antigen receptor of claim 13, wherein the intracellular signaling domain is a T cell receptor intracellular signaling domain.

15. The chimeric antigen receptor of claim 13, further comprising a transmembrane domain or an intracellular signaling domain of a costimulatory protein receptor, and/or the chimeric receptor further comprises a hinge domain.

16. A recombinant immune cell comprising the chimeric antigen receptor claim 13.

17. A bi-specific T-cell engager comprising (a) an antigen-binding antibody fragment of claim 1, and (b) an antigen binding domain that binds to a T-cell antigen.

18. A method, comprising administering an effective amount of the antibody, or antigen-binding antibody fragment of claim 1, or a bi-specific T-cell engager or a chimeric antigen receptor comprising said antibody, or antigen-binding antibody fragment to a subject in need thereof, wherein said subject has a disease characterized by B7-H6-expressing cells.

19. The method of claim 18, wherein (i) the effective amount is an amount effective to kill or reduce, in a subject, growth of cells expressing B7 homolog 6; (ii) the effective amount is an amount effective to kill or reduce, in a subject, growth of cancer cells expressing B7 homolog 6; (iii) the subject has myeloid leukemia, acute nonlymphocytic leukemia, acute lymphoblastic leukemia, B-cell lymphoma, breast cancer, cervical cancer, clear cell renal cell carcinoma, dermatofibrosarcoma protuberans, gastric sarcoma, gastrointestinal stromal tumor, glioblastoma, leiomyosarcoma, invasive ductal breast carcinoma, malignant fibrous histiocytoma, melanoma, ovarian serous surface papillary carcinoma, pancreatic cancer, prostate cancer, T-cell acute lymphoblastic leukemia or T-cell lymphoma; (iv) the effective amount is an amount effective to induce an immune response, in the subject, against cells expressing B7 homolog 6; (v) the subject has an autoimmune disorder; (iv) the subject has Sjogren's syndrome; and/or (vi) the method includes co-administering a second therapeutic agent.

20. The method of claim 18, wherein said antibody or antigen-binding antibody fragment, or a bi-specific T-cell engager or a chimeric antigen receptor comprising said antibody or antigen-binding antibody fragment is expressed by a recombinant cell.

21. The chimeric antigen receptor of claim 15, wherein the hinge domain is a CD28 or CD8 hinge region.

* * * * *